United States Patent [19]

Vyas et al.

[11] Patent Number: 4,487,769

[45] Date of Patent: Dec. 11, 1984

[54] AMIDINES

[75] Inventors: Dolatrai M. Vyas; Takushi Kaneko; Terrence W. Doyle, all of Fayetteville, N.Y.

[73] Assignee: Bristol-Myers Company, New York, N.Y.

[21] Appl. No.: 492,903

[22] Filed: May 9, 1983

Related U.S. Application Data

[63] Continuation-in-part of Ser. No. 385,149, Jun. 4, 1982, abandoned.

[51] Int. Cl.$^3$ .................... A61K 31/40; C07D 403/04
[52] U.S. Cl. .................... 424/246; 260/245.7; 424/248.54; 424/267; 424/274; 544/58.5; 544/142; 546/199; 548/422
[58] Field of Search .................... 548/422; 260/245.7; 544/58.5, 142; 546/199; 424/246, 248.54, 267, 274

[56] References Cited

U.S. PATENT DOCUMENTS

| | | |
|---|---|---|
| 3,121,084 | 2/1964 | Winberg ................ 260/268 |
| 3,332,944 | 7/1967 | Cosulich et al. ............. 548/422 X |
| 3,420,846 | 1/1969 | Matsui et al. ................ 548/422 |
| 3,450,705 | 6/1969 | Matsui et al. ................ 548/422 X |
| 3,514,452 | 5/1970 | Matsui et al. ................ 260/240 |
| 3,660,578 | 5/1972 | Hata et al. .................... 424/274 |
| 4,231,936 | 11/1980 | Nakano et al. ............... 548/422 |
| 4,268,676 | 5/1981 | Remers ........................ 548/181 |

FOREIGN PATENT DOCUMENTS 6073085  11/1979  Japan .

OTHER PUBLICATIONS

Webb et al., JACS, vol. 84, (1962), pp. 3185–3187.
Matsui et al., J. Antibiotics, vol. XXI, (1968), pp. 189–198.
Kinoshita et al., J. Med. Chem., vol. 14, (1971), pp. 103–109.
Sandler et al., Org. Chem., vol. 12, (1972), pp. 227 and 228.
Abdulla et al., Tetrahedron, vol. 35, (1979), pp. 1720–1724.
Iyengar et al., J. Med. Chem., vol. 24, (1981), pp. 975–981.
Iyengar et al., Abstracts of Papers, Annual Meeting of the American Chemical Society, Las Vegas, Mar. 1982, #MEDI 72.

*Primary Examiner*—Richard L. Raymond
*Attorney, Agent, or Firm*—Robert E. Carnahan

[57] ABSTRACT

Mitomycin A, mitomycin C, and porfiromycin react with amide acetals and other amide derivatives to produce amidine derivatives having antitumor activity against experimental animal tumors. The amidines derived from mitomycin C are useful intermediates in reactions with primary amines to produce both known and novel 7-amino-9a-methoxymitosanes having antitumor activity against experimental animal tumors.

39 Claims, No Drawings

AMIDINES

REFERENCE TO RELATED APPLICATION

This application is a continuation-in-part of our co-pending application Ser. No. 385,149 filed June 4, 1982, and now abandoned.

FIELD OF THE INVENTION

The present invention refers to mitomycin analogs containing one or more amidino groups (Class 260 Subclass 326.24). These compounds are mitomycin C derivatives in which either, or both, of the 7-amino group and carbamido nitrogen atom are incorporated within an amidino substituent. These compounds are active antitumor substances in experimental animal tumors.

Nomenclature.—The systematic Chemical Abstracts name for mitomycin C is:
[1aR-(1aα,8β,8aβ,8aβ, 8bα)]-6-amino-8-[((aminocarbonyl)oxy)methyl]-1,1a,2,8,8a,8b-hexahydro-8a-methoxy-5-methyl-azirino[2',3',3,4]-pyrrolo[1,2-a]indole-4,7-dione
according to which the azirinopyrroloindole ring system is numbered as follows:

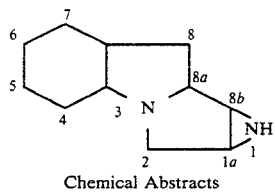

Chemical Abstracts

A trivial system of nomenclature which is found wide use in the mitomycin literature identifies the foregoing ring system including several of the characteristic substituents of the mitomycins as mitosane.

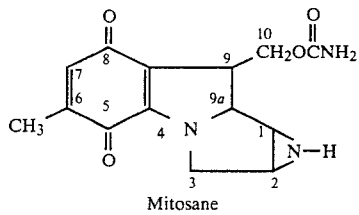

Mitosane

While this system is convenient and appropriate for a number of simple derivatives such as those bearing N-substituents on the azirino ring nitrogen atom or in the 7- or 9a-positions, it suffers from certain ambiguities and shortcomings for general use. With regard to the compounds of the present invention some of which have substituents on both the azirino ring nitrogen atom and on the side chain carbamoyl nitrogen atom, there is no conventional numbering to distinguish these positions. Therefore, we have chosen in the present specification to refer to the azirino nitrogen atom as $N^{1a}$ and the carbamoyl nitrogen atom as $N^{10}$ in using the mitosane nomenclature system. As to the stereochemical configuration of the products of this invention, it is intended when identifying them by the root name "mitosane" or by structural formula to identify the stereochemical configuration thereof as the same as that of mitomycin C.

DESCRIPTION OF THE PRIOR ART

Mitomycin C is an antibiotic which is produced by fermentation and is presently on sale under Food and Drug Administration approval in the therapy of disseminated adenocarcinoma of the stomach or pancreas in proven combinations with other approved chemotherapeutic agents and as palliative treatment when other modalities have failed (Mutamycin ® Bristol Laboratories, Syracuse, N.Y. 13201, Physicians'Desk Reference 35th Edition, 1981, pp. 717 and 718). Mitomycin C and its production by fermentation is the subject of U.S. Pat. No. 3,660,578 patented May 2, 1972 claiming priority from earlier applications including an application filed in Japan on Apr. 6, 1957.

The structures of mitomycins A, B, C, and of porfiromycin were first published by J. S. Webb et al. of Lederle Laboratories Division American Cyanamid Company, J. Amer. Chem. Soc. 84, 3185–3187 (1962). One of the chemical transformations used in this structure study to relate mitomycin A and mitomycin C was the conversion of the former, 7-9α-dimethoxymitosane, by reaction with ammonia to the latter, 7-amino-9α-methoxymitosane. Displacement of the 7-methoxy group of mitomycin A has proven to be a reaction of considerable interest in the preparation of antitumor active derivatives of mitomycin C. The following articles and patents each deal with the conversion of mitomycin A to a 7-substituted amino mitomycin C derivative having antitumor activity. The object of this research was to prepare derivatives which were more active, and particularly which were less toxic than mitomycin C:

Matsui et al. "The Journal of Antibiotics", XXI, 189–198 (1968).
Kinoshita et al. "J. Med. Chem." 14, 103–109 (1971).
Iyengar et al. "J. Med. Chem." 24, 975–981 (1981).
  Iyengar, Sami, Remers, and Bradner, Abstracts of Papers Annual Meeting of the American Chemical Society, Las Vegas, Nev., March 1982, Abstract No. MEDI 72.

The following patents deal with the preparation of 7-substituted aminomitosane derivatives by the reaction of mitomycin A, mitomycin B, or an $N^{1a}$- substituted derivative thereof with a primary or secondary amine:

Cosulich et al. U.S. Pat. No. 3,332,944 patented July 25, 1967.
Matsui et al. U.S. Pat. No. 3,420,846 patented Jan. 7, 1969.
Matsui et al. U.S. Pat. No. 3,450,705 patented June 17, 1969.
Matsui et al. U.S. Pat. No. 3,514,452 patented May 26, 1970.
Nakano et al. U.S. Pat. No. 4,231,936 patented Nov. 4, 1980.
Remers U.S. Pat. No. 4,268,676 patented May 19, 1981.

Mitomycin C derivatives having a substituted amino substituent in the 7-position have also been prepared by directed biosynthesis, that is by supplementing fermentation broths with a series of primary amines, and carrying out the conventional mitomycin fermentation (C. A. Claridge et al. Abst. of the Annual Meeting of Amer. Soc. for Microbiology 1982. Abs. 028).

Mitomycin C is the principal mitomycin produced by fermentation and is the commercially available form. Current technology for the conversion of mitomycin C to mitomycin A for use in the production of the semi-synthetic substituted amino analogs of mitomycin C referred to in the foregoing publications involves hydrolysis of mitomycin C to the corresponding 7-hydroxymitosane, a highly unstable compound, and then methylation of that substance with diazomethane which is a very hazardous substance to handle. One attempt to avoid the use of diazomethane for methylation of the 7-O-demethyl mitomycin A which is produced by hydrolysis of mitomycin C involves the use of 7-acyloxymitosanes (Kyowa Hakko Kogyo KK Japanese Patent No. J5 6073-085, Farmdoc No. 56227 D/31).

SUMMARY OF THE INVENTION

The present invention is concerned with a novel group of monoguanidino, or mono- and bis-amidino analogs of mitomycin C in which either or both the 7-amino nitrogen atom and the $N^{10}$ carbamoyl nitrogen atom of mitomycin C are part of an amidino substituent or the 7-amino nitrogen is part of a guanidino group. Corresponding analogs of mitomycin A having the methoxy group in the 7-position and the amidino group at the $N^{10}$- position are also included. The compounds of the present invention conform to the following structural formula:

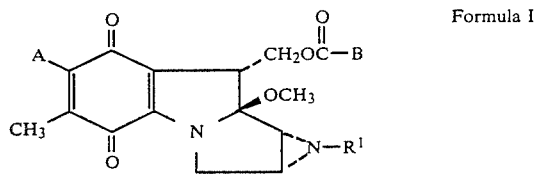

Formula I

Wherein:

A is amino, methoxy, hydroxy, (1-lower alkyl-2-(1H)-pyridinylidene)amino, or a group of the formula

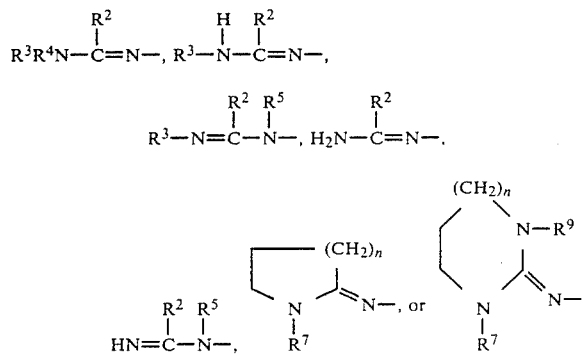

B is amino or the amidino group of the formula

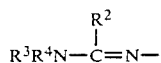

and at least one of A and B is one of the specified groups other than amino, methoxy, or hydroxy,
n is the integer of 0, 1, 2, or 3,
$R^1$ is hydrogen, lower alkyl, lower alkyanoyl, benzoyl or substituted benzoyl wherein said substituent is lower alkyl, lower alkoxy, halo, amino, or nitro,
$R^2$ is hydrogen, lower alkyl, phenyl, lower alkylphenyl, lower alkoxyphenyl, halophenyl, aminophenyl, nitrophenyl, thienyl, furyl, cyano, dilower alkylamino, lower alkoxy, or lower alkylthio,
$R^3$ is lower alkyl, lower alkoxy, or together with $R^4$ and the nitrogen atom to which they are attached constitutes pyrrolidine, 2-, or 3-lower alkylpyrrolidine, piperidine, 2-, 3-, or 4-lower alkylpiperidine, 2,6-dilower alkylpiperidine, piperazine, 4-substituted piperazine (wherein said 4-substituent is alkyl, or cabalkoxy each having 1 to 8 carbon atoms, phenyl, methylphenyl, methoxyphenyl, halophenyl, nitrophenyl, or benzyl), azepine, 2-, 3-, 4-, or 5-lower alkylazepine, morpholine, thiomorpholine, thiomorpholine-1-oxide, or thiomorpholine -1,1-dioxide.
$R^4$ is lower alkyl, or together with $R^3$ and the nitrogen atom to which they are attached constitutes pyrrolidine, 2-, or 3-lower alkylpyrrolidine, piperidine, 2-, 3-, or 4-lower alkylpiperidine, 2,6-dilower alkylpiperidine, piperazine, 4-substituted piperazine (wherein said 4-substitutuent is alkyl, or carbalkoxy each having 1 to 8 carbon atoms, phenyl, methylphenyl, methoxyphenyl, halophenyl, nitrophenyl, or benzyl), azepine, 2-, 3-,4-, or 5-lower alkylazepine, morpholine, thiomorpholine, thiomorpholine-1-oxide, or thiomorpholine-1,1- dioxide.
$R^5$ is selected from $C_{1-18}$ alkyl other than tert.-alkyl, $C_{1-18}$ alkenyl, $C_{1-18}$ alkynyl, $C_{1-18}$ haloalkyl, $C_{1-18}$ hydroxyalkyl, $C_{4-8}$ cycloalkyl, or aryl or lower aralkyl, each having up to 12 carbon atoms or a heteroalicyclic or heteroaromatic group having from 3 to 8 ring members at least two of which are carbon atoms,
$R^7$ and $R^9$ are independently H or lower alkyl
wherein each of the aforesaid lower alkyl, lower alkanoyl and lower alkoxy groups contains 1 to 6 carbon atoms.

Those skilled in the art will recognize that tautomeric forms of some of the foregoing amidino group exist. Such are also intended to be covered by the foregoing formulas, and the present invention.

The foregoing substances of formula I have antitumor activity in experimental animals. They are also useful as intermediates for preparing other compounds having antitumor activity in animals. The present invention includes methods for preparing the foregoing substances and for their transformation into other useful compounds having antitumor activity in experimental animals as is described below.

The process of the present invention which employs the foregoing substances as intermediates to prepare other compounds having antitumor activity in animals involves reaction of a compound of Formula I wherein A or both A and B are the said amidino group with a primary amine resulting in cleavage of the $N^{10}$-aminomethylene substituent, when present, with conversion thereof to the $NH_2$ group as is present in mitomycin A and mitomycin C. The primary amines, with certain exceptions, react also at position 7 by displacement of the amidino group and replacement thereof with the amino substituent corresponding to the reactant. These processes are illustrated in the following equations:

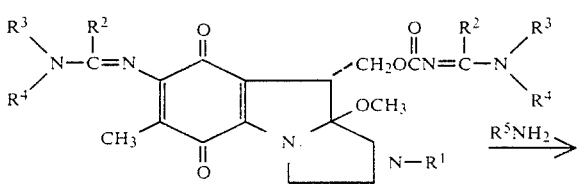

Formula II

-continued

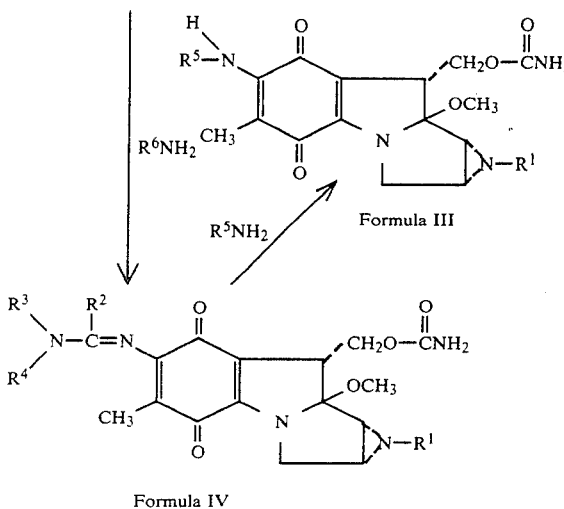

Formula III

Formula IV $R^5$ representing the nitrogen substituent of various known and novel 7-substituted amino mitomycin C compounds and of the primary amines capable of displacement of the 7-amidino group of Formula II is selected from $C_{1-18}$ alkyl other than tert.-alkyl, $C_{1-18}$ alkoxy, $C_{1-18}$ alkenyl, $C_{1-18}$ alkynyl, $C_{1-18}$ haloalkyl, $C_{1-18}$ hydroxyalkyl, $C_{4-8}$ cycloalkyl, aryl or lower aralkyl or lower aralkoxy each having up to 12 atoms, or a heteroalicyclic or heteroaromatic group having from 3 to 8 ring members at least two of which are carbon atoms. $R^6$ representing the nitrogen substituent of the primary amines capable only of cleaving the $N^{10}$ amidino substituent is the residue of a very weakly basic aliphatic amine or a highly hindered alkylamine or aralkylamine. Examples are trifluoroethylamine, benzhydrylamine (i.e. aminodiphenylmethane), or tert.-butyl-amine.

The compounds of Formula I are prepared by reaction of mitomycin C, 7-hydroxy-9a-methoxymitosane, or mitomycin A or an $N^{1a}$-substituted analog of any of the foregoing with an amide acetal. Those compounds of Formula I wherein A, but not B, is said amidino group may also be prepared by reaction of mitomycin C or an $N^{1a}$-substituted analog thereof with a strong base to form an anion at $N^7$ followed by reaction of the anion with a reagent capable of generating the aminomethylene group such as a halomethyleniminium salt.

DETAILED DESCRIPTION OF THE INVENTION

The preferred compounds of the present invention are mitomycin C analogs in which the 7-amino group is incorporated into a substituted or unsubstituted amidino group. They have strong antitumor action against experimental animal tumors. These compounds are prepared by reaction of mitomycin C with a reagent capable of transforming the 7-amino group into a 7-amidino group. Preferred reagents for this purpose are the amide acetals which react in good yield and under mild conditions with mitomycin C (Examples 1-5, and 18). Another group of amidine forming reagents are the imidoyl halides (Example 17), halomethyleniminium salts (Example 15), 2-halo-1-alkylpyridinium halides (Example 16), and iminoethers or iminothioethers (Examples 13 and 14) which react with the anionic form of mitomycin C formed by deprotonation of the 7-amino group thereof by treatment with strong base. Conditions for the deprotonation of mitomycin C involve treatment of mitomycin C in dimethylformamide solution with about 1.5 molar proportions of sodium hydride at room temperature. The reaction of the anionic form so produced with one of the foregoing reagents preferably employs from 1 to 1.5 molar proportions thereof relative to the mitomycin C at a temperature of from room temperature to about $-60°$ C. Aprotic polar organic solvents such as dimethylformamide, hexamethylphosphoramide, dimethyl sulfoxide, or pyridine are utilized as reaction medium. The method is not, however, limited to formation of anionic mitomycin C in this specific fashion, since modifications will occur to those skilled in the art.

The preferred method for preparing the compounds of formula I wherein B or each of A and B is the amidino group of the formula

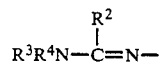

is by reaction of mitomycin C or mitomycin A or an $N^{1a}$-substituted derivative of either with an amide acetal of the formula

Formula V wherein $R^2$, $R^3$ and $R^4$ are defined as above $R^8$ is lower-alkyl, or cycloalkyl having up to 6 carbon atoms or the two $R^8$ groups are joined as an alkylene chain forming with the two oxygen atoms and intervening carbon atom a cyclic structure having 5 or 6 ring members. The reaction of such amide acetals, with amines, is quite well known in the art, and those skilled in the art will know how to conduct the reaction with mitomycin C, mitomycin A, or the $N^{1a}$ alkyl derivatives thereof. Refer, for instance, to H. E. Winberg U.S. Pat. No. 3,121,084 (Feb. 11, 1964), and to R. F. Abdulla et al. "The Chemistry of Formamide Acetals", Tetrahedron, Vol. 35 pp. 1720-24 (1979).

We prefer to carry out the reaction in a liquid anhydrous reaction medium in which the diluent is a liquid which is compatible with the reaction conditions. Preferably, the latter is a lower halogenated aliphatic hydrocarbon or a lower alkanol or desirably a mixture of the two. Chloroform and methanol and mixtures thereof are quite suitable. The reaction is carried out at a temperature of from 40° to 65° C. for a sufficient length of time for the reaction to go to completion.

When a large excess (~60 fold) of the acetal is employed, the predominant product formed is the bis-amidino product, that is those substances of formula I wherein both A and B comprise the amidino group. The $N^{1a}$-formyl derivative is sometimes formed as a by-product. However, with a limited amount (~10 fold) of the acetal, in addition to the bis-amidino product, a mono amidino product i.e. a product of formula I where A is the amino group, and B is the amidino group is also produced. Mixtures of the foregoing reaction products are readily separated by chromatography as is described in the examples which follow.

Some commerically available amide acetals which may be used in this process are listed in Table I which is taken from the cited Abdulla et al. article, p. 1685.

TABLE I

| Some Commercially Available Amide Acetals | |
|---|---|
| Acetal | Structure |
| A | $(CH_3)_2NCH(OCH_3)_2$ |
| B | $(CH_3)_2NCH(OCH_2CH_3)_2$ |
| C | $(CH_3)_2NCH(OCH_2-\underset{\underset{CH_3}{\mid}}{\overset{\overset{CH_3}{\mid}}{C}}-CH_3)_2$ |
| D | $(CH_3)_2NC(CH_3)(OCH_3)_2$ |
| E | 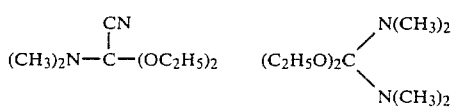 |
| F | $(CH_3)_2NCH(O-CH\underset{CH_3}{\overset{CH_3}{<}})_2$ |
| G | $(CH_3)_2NCH(OCH_2CH_2CH_3)_2$ |
| H |  |

The substances of formula I in which $R^2$ is cyano, dilower alkylamino, lower alkoxy, or lower alkylthio are prepared by substitution of the following orthocarbonate derivatives for the amide acetals in the foregoing process.

$(CH_3)_2N-\underset{\underset{CN}{\mid}}{C}-(OC_2H_5)_2$     $(C_2H_5O)_2C\underset{N(CH_3)_2}{\overset{N(CH_3)_2}{<}}$ Formula VI         Formula VII $(C_2H_5O)_3C-N(CH_3)_2$     $(C_2H_5S)_3C-N(CH_3)_2$ Formula VIII         Formula IX These reagents are available from the following sources:
Formula VI: Kantlehner, et al., Liebigs Ann. Chem., 1981, 70–84.
Formula VII, VIII and IX: H. Meerwein, et al., Liebigs Ann. Chem. 641, 1 (1961).

The amidino derivatives of formula I wherein A is

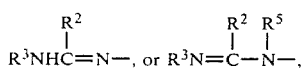

are prepared from the anionic form of mitomycin C or an $N^7$-substituted derivative thereof as described above. Suitable halomethyleniminium salts for use in this process have been described in the literature. Representative are those listed by W. Kantlehner in "Advances in Organic Chemistry", Vol. 9, Part 2, Wiley Interscience, 1979, pp. 81 and 82. Table II which follows is taken from the Kantlehner summary.

TABLE II

Halomethyleniminium Salts $R^2-\underset{\overset{\oplus}{NR^3R^4}}{\overset{X}{C}}\quad Y^\ominus$

| $R^2$ | $R^3$ | $R^4$ | X | Y | m.p., °C. |
|---|---|---|---|---|---|
| H | $CH_3$ | $CH_3$ | Cl | Cl | 140–145 |
| H | $CH_3$ | $CH_3$ | Br | Br | 156–158 |
| H | $CH_3$ | $CH_3$ | I | I | 110 |
| H | —$(CH_2)_5$— | | Cl | Cl | 58–66 |
| H | $CH_3$ | $C_6H_5$ | Cl | Cl | Oil |
| $CH_3$ | $CH_3$ | $CH_3$ | Cl | Cl | 150–120 |
| $C_2H_5$ | $CH_3$ | $CH_3$ | Cl | Cl | 68–70 |
| $C_2H_5$ | —$(CH_2)_5$— | | Cl | Cl | 82–85 |
| n-$C_3H_7$ | $CH_3$ | $CH_3$ | Cl | Cl | 82–84 |
| n-$C_3H_7$ | $C_2H_5$ | $C_2H_5$ | Cl | Cl | 20 |
| i-$C_3H_7$ | $C_2H_5$ | $C_2H_5$ | Cl | Cl | 20 |
| n-$C_4H_9$ | $CH_3$ | $CH_3$ | Cl | Cl | 50–55 |
| —$(CH_2)_3$— | | $CH_3$ | Cl | Cl | 75–79 |
| $C_6H_5$ | $CH_3$ | H | Cl | Cl | 93–95 |
| $C_6H_5$ | $CH_3$ | H | Cl | Br | 115–117 |
| $C_6H_5$ | $CH_3$ | D | Cl | Br | 115–118 |
| $C_6H_5$ | $CH_3$ | $CH_3$ | Cl | Cl | 95–96 |
| $C_6H_5$ | —$(CH_2)_5$— | | Cl | Cl | 136–140 |
| $C_6H_5$ | —$(CH_2)_4$— | | Br | $Br_3$ | 64 |
| $C_6H_5$ | —$(CH_2)_5$— | | Br | $Br_3$ | 97 |
| $C_6H_5$ | —CH—$(CH_2)_4$—CH—<br>    $\|$                 $\|$<br>    $CH_3$          $CH_3$ | | Br | $Br_3$ | 125 |
| $C_6H_5$ | —CH—$(CH_2)_3$—CH—<br>    $\|$                 $\|$<br>    $CH_3$          $CH_3$ | | Br | $Br_3$ | 124 |
| $C_6H_5$ | $CH_3$ | $CH_3$ | Br | Br | 120 (dec) |
| $C_6H_5$ | —$(CH_2)_4$— | | Br | Br | 178 (dec) |
| $C_6H_5$ | —$(CH_2)_6$— | | Br | Br | 195 (dec) |
| $C_6H_5$ | —CH—$(CH_2)_4$—<br>    $\|$<br>    $CH_3$ | | Br | Br | 160 |
| $C_6H_6$ | —CH—$(CH_2)_3$—CH—<br>    $\|$                 $\|$<br>    $CH_3$          $CH_3$ | | Br | Br | — |
| $C_6H_5$ | —CH—$(CH_2)_4$—<br>    $\|$<br>    n-$C_3H_7$ | | Br | Br | 85–95 |
| p-$OCH_3$—$C_6H_4$ | —$(CH_2)_5$— | | Cl | Cl | 85 |
| p-$NO_2$—$C_6H_4$ | $CH_3$ | $CH_3$ | Cl | Cl | 90 (dec) |
| p-$NO_2$—$C_6H_4$ | —$(CH_2)_5$— | | Cl | Cl | 117–119 |
| | $CH_3$ | H | Cl | Cl | 103–104 |
| | $CH_3$ | H | Cl | Br | 132–134 (dec) |
| | $CH_3$ | D | Cl | Cl | 103–105 |
| | $CH_3$ | D | Cl | Br | 133–134 (dec) |
| | $C_2H_5$ | H | Cl | Cl | 93–94 |
| | $C_2H_5$ | H | Cl | Br | 151–152 |
| | $CH_3$ | $CH_3$ | Cl | Cl | 181–182 |
| | $C_2H_5$ | $C_2H_5$ | Cl | Cl | 99–103 |

When using a halomethyleniminium salt as reactant as illustrated in Table II, it is sometimes convenient to use the corresponding amide as solvent, that is the amide from which the iminium salt was prepred. In cases where the corresponding amides are solid, hexamethylphosphoramide or pyridine may be used. This is illustrated in Examples 17 and 19 below.

The imidoyl chlorides derived from N-substituted formamides are also convenient reactants for this purpose. Their preparation is well established in the art as illustrated in Table III which is taken from H. Ulrich in "The Chemistry of Imidoyl Halides", Plenum Press, New York, 1968, pp. 74–76. Their reaction with amines to form amidines is also well established as illustrated by S. R. Sandler and W. Karo in "Organic Chemistry", Vol. 12-III, A. T. Blomquist and H. Wasserman, editors, Academic Press, New York, 1972, p. 227.

TABLE III

Imidoyl Chlorides $$R^2-\underset{Cl}{\underset{|}{C}}=NR^3$$

| $R^2$ | $R^3$ | B.p., °C./mm (M.p., °C.) |
|---|---|---|
| $CH_3$ | $C_6H_{11}$ | 45–56/0.04 |
|  | $C_6H_5$ | (118–120) |
|  | 2-$CH_3C_6H_4$ | 60/0.1 |
|  | 2-$FC_6H_4$ | 70/0.25 |
|  | 2-$ClC_6H_4$ | 111–114/14 |
|  | 2-$BrC_6H_4$ | 142–143/12 |
| $C_2H_5$ | $C_6H_{11}$ | 43–44/0.02 |
| $CH_3CH_2CCl_2$ | $C_2H_5$ | 72–75/14 |
| $(CH_3)_2CH$ | $C_6H_{11}$ | 40–41/0.001 |
|  | 2-$CH_3C_6H_4$ | 67/0.3 |
|  | 4-$CH_3C_6H_4$ | 80–85/0.8 |
|  | 4-$CH_3OC_6H_4$ | 93–94/0.25 |
| $n\text{-}C_4H_9(C_2H_5)CH$ | $n\text{-}C_4H_9$ | 72–76/0.7 |
| $(CH_3)_3C$ | $C_6H_{11}$ | 104–106/20 |
| $C_6H_{10}Cl$ | $C_2H_5$ | 102/3 |
| $C_6H_5$ | $CH_3$ | 46–47/2 |
|  |  | 90–92/13 |
|  | $C_2H_5$ | 47–48/1 |
|  | i-$C_3H_7$ | 52–54/1 |
|  | n-$C_4H_9$ | 85–86/1 |
|  | $C_6H_{11}$ | 110–112/1 (66–67) |
|  | $CH_2C_6H_5$ | 128–130/1 |
|  | $C_6H_5$ | 175–176/12 (40–41) |
|  | 2,6-$(CH_3)_2C_6H_3$ | 153–156/1 |
|  | 2-$CH_3OC_6H_4$ | 188–190/6 |
|  | 4-$CH_3OC_6H_4$ | 198–200/20 (61–63) |
|  | 2,4-$(O_2N)_2C_6H_3$ | (122–124) |
| 2-$CH_3C_6H_4$ | $C_6H_5$ | 174–177/10 |
| 4-$CH_3C_6H_4$ | $C_6H_5$ | 141–144/1 (40–41) |
| 4-$ClC_6H_4$ | $C_6H_5$ | (66–67) |
| 4-$BrC_6H_4$ | 4-$BrC_6H_4$ | (93–94) |
| 4-$CH_3OC_6H_4$ | $C_6H_5$ | 183–185/3 (73–76) |
| 4-$O_2NC_6H_4$ | $C_6H_{11}$ | (40–42) |
|  | $C_6H_5$ | (137–138) |
|  | 4-$O_2NC_6H_4$ | (132–134) |
| 3,5-$(O_2N)_2C_6H_3$ | $C_6H_{11}$ | (86–87) |
| 2,4,6-$(CH_3)_3C_6H_2$ | $C_6H_5$ | 164–165/1 (60–62) |

The substances of formula I wherein A is the nitrogen unsubstituted amidino group,

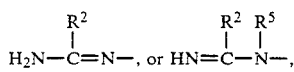

are prepared by reaction of an amino-protected imino ether with mitomycin C, an $N^7$-substituted derivative thereof, or an $N^{1a}$-lower alkyl derivative of either in the anionic form in the fashion described above. The protecting group is then removed in conventional fashion. Isopropylformimidate in which the amino group is protected by the β-trimethylsilylethoxycarbonyl group is a suitable reactant (Example 13).

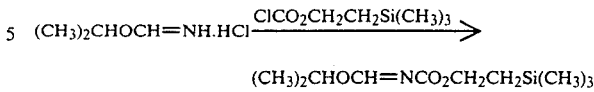

When A is (1-lower alkyl-2(1H)-pyridinylidene)amino or the group of the formula

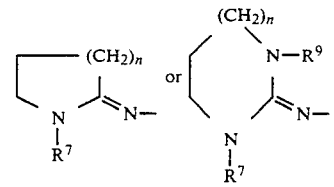

the preparative procedures involve reaction of the anionic form of mitomycin C with cyclic halomethylleniminium salts or imidoyl halides in which $R^2$ and $R^3$ of the formula

are joined to form a ring. Suitable reagents for reaction with the mitomycin C anion are 2-chloro-1-methylpyridinium iodide (Example 16), 2-chloro-4,5-dihydro-1-methyl-1(3H)-pyrrolidinium chloride (Table II), N,N'-dimethyl-N,N'-trimethylenechloroformamidimium chloride (Example 28) and other cyclic imidoyl halides derived from 2-azetidinones, 2-pyrrolidinones, 2-piperidinones, and 2-azepinones. Again, when $R^7$ or $R^9$ of the final product is hydrogen, a protecting group such as above is employed in the intermediate cyclic halomethyleneiminium salt.

The substances of formula I wherein A or both A and B are an amidino group of the formula

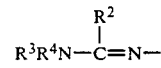

react with primary amines of the formula $R^5NH$ in which $R^5$ is selected from $C_{1-18}$ alkyl other than tert.-alkyl, $C_{1-18}$ alkenyl, $C_{1-18}$ alkynyl, $C_{1-18}$ haloalkyl, $C_{1-18}$ hydroxyalkyl, $C_{4-8}$ cycloalkyl, or aryl or lower aralkyl, each having up to 12 carbon atom or a heteroalicyclic or heteroaromatic group having from 3 to 8 ring members at least two of which are carbon atoms. The only limitation on the choice of primary amine, other than the absence of functional groups which are incompatible with the reaction conditions, is that the amino nitrogen atom is attached to a carbon atom which bears at least one hudrogen atom, and less than two aryl groups. An anhydrous liquid organic compound is employed as reaction medium and any such substance may be employed so long as it is compatible with the reaction conditions, and does not participate in the reaction in a deleterious way. An excess of the primary amine reactant, on a molecular basis, is generally employed. A reaction temperature in the range of from about −15° C. to +50° C. is preferred. The product resulting from this reaction is a 7-substiuted amino-9α-methoxymitosane, namely a mitomycin C derivative bearing a substituent as defined for $R^5$ on the 7-amino group. Such compounds are known from the prior art to possess a substantial degree of antitumor activity in experimental animals.

Some primary amines, designted by the formula $R^6NH_2$, have been found to be incapable of displacing the 7-amidino group according to the process described in the preceding paragraph. $R^6$ is alkyl, cyclo-alkyl, cycloalkylalkyl, aralkyl, or heteroalicyclic having from 4 to 8 carbon atoms in which the carbon atom bearing the amino group is a tertiary carbon atom or a secondary carbon atom bearing 2 aryl groups. Certain other weakly basic aliphatic amines such as trifluoroethylamine also fail to displace the 7-amidino group. These amines are useful for transforming a compound of formula I in which both A and B are the said amidino group of the formula

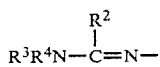

to a compound of formula I wherein only A is the said amidino group. These amines, while lacking the ability to displace the 7-amidino group, nevertheless have the capacity to cleave the amidino group designated B to $NH_2$ to provide the carbamido function characteristic of the unsubstituted mitosanes. The amine itself may serve as reaction medium or a solvent system as defined in the preceding paragraph may be employed. This process is preferably carried out in the reaction range of from 20° C. to 60° C.

DESCRIPTION OF SPECIFIC EMBODIMENS

Melting points were recorded on a Thomas-Hoover capillary melting point apparatus and are uncorrected. Temperatures are expressed in degrees Centigrade. Proton nuclear magnetic resonance (NMR) spectra were recorded on a Varian XL100 spectrometer in pyridine-$d_5$ unless otherwise stated. Infra red (IR) spectra were obtained with a Beckman 4240 spectrophotometer and the sample compressed into a pellet with potassium bromide. IR figures are $\nu_{max}$ in cm$^{-1}$. UV-visible spectra were recorded on a Varian-Cary 219 spectrophotometer.

Thin layer chromatography (tlc) was carried on 0.25 mm precoated silica gel plates using UV light as visualizing agent. Flash chromatography was performed using Silica Woelm (32–63 μm). Solvents were evaporated under reduced pressure and below 50° C.

EXAMPLE 1

COMPOUND V
7-[(Dimethylamino)methylene]amino-$N^{10}$-(dimethylamino)methylene-9a-methoxymitosane
Compound VI
7-[(Dimethylamino)methylene]amino-$N^{10}$-(dimethylamino)methylene-$N^{1a}$-formyl-9a-methoxymitosane

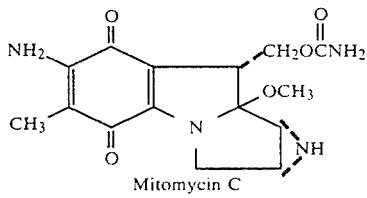
Mitomycin C

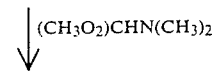

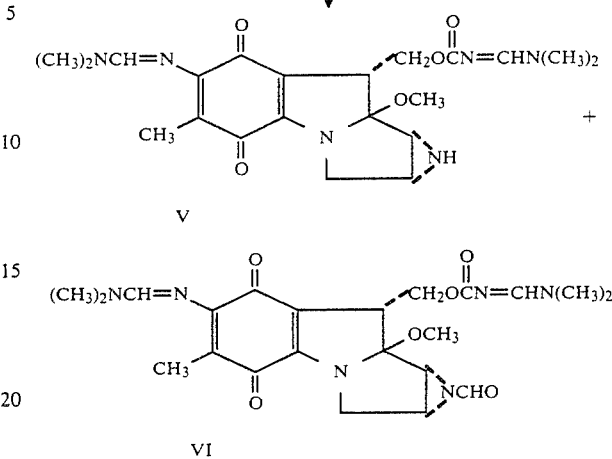

To a suspension of 500 mg (1.50 mM) of mitomycin C in 25 ml chloroform was added in total 9.6 ml (2.4 ml portions at 0, 18, 21 and 23 hrs) of N,N-dimethylformamide dimethyl acetal and the suspension was stirred at about 50° for 41 hrs. Upon evaporation of the solvent and excess reagent under reduced pressure, a dark green residue was obrained; tlc (methylene chloride/methanol 20:1) revealed the absence of mitomycin C and the presence of two new green components (Rf=0.16 and 0.22). The major component (Rf=0.16) was isolated by flash chromatography; using methylene chloride/methanol 20:1 as the eluant, as a green solid (340 mg 51.5%), which upon dissolution in diethyl ether followed by an addition of hexane afforded Compound V as a dark green amorphous powder.

NMR (pyriding $d_5$, δ); 2.18 (s, 3H), 2.70 (bs, 1H), 2.76 (s, 3H), 2.82 (s, 3H), 2.86 (s, 6H), 3.22 (s, 3H), 3.30 (bs, 1H), 3.60 (d, J = 12 Hz). 4.12 (dd, 1H, J = 10, 4 Hz), 4.43 (d, 1H, J = 12 Hz), 4.90 (bs, 1H), 5.10 (t, 1H, J = 10 Hz), 5.52 (dd, 1H, J = 10, 4 Hz), 7.85 (s, 1H), 8.64 (s, 1H).

IR (KBr) $\nu_{max}$, cm$^{-1}$: 3300, 2930, 1675, 1620, 1545, 1230, 1060.

UV($H_2O$) $\lambda_{max}$, nm: 390 and 244.

Analysis: Calc'd for $C_{21}H_{28}N_6O_5$; :C, 56.71; H, 6.08; N, 18.90. Found: C. 56.20; H. 6.28; N, 7.88.

The minor component (Rf=0.22), isolated (180 mg, 25.35%) as an amorphous solid upon precipitation from diethyl ether and hexane was identified as Compound VI.

NMR (pyridine $d_5$, δ): 2.20 (s, 3H), 2.60–3.00 (3 singlets, 12H), 3.2 (s, 3H), 3.65 (m, 2H), 4.04 (d, 1H, J = 4 Hz), 4.16 (dd, 1H, J = 12, 4 Hz), 4.60 (d, 1H, J = 13 Hz), 4.86(t, 1H, J = 12 Hz), 4.90 (s, 1H), 5.48 (dd, 1H, J = 12, 4 Hz), 7.90 (s, 1H), 8.64

(s, 1H), 9.06 (s, 1H). IR (KBr) $\nu_{max}$, cm$^{-1}$: 2490, 2860, 1698, 1630, 1600, 1540, 1250, 1060.

UV($H_2O$), $\lambda_{max}$, nm: 390 and 244.

Analysis: Calc'd for $C_{22}H_{28}N_6O_6$: C, 55.89; H, 5.93; N, 17.78. Found: C, 55.41, H, 5.96; N, 16.99.

Solutions of Compounds V and VI in either ethyl acetate or N,N-dimethyl formamide dimethyl acetal upon standing at room temperature for >10 hrs revealed by tlc that Compound VI (Rf=0.22) was converting to Compound V (Rf=0.16) to give a solution highly enriched in the latter.

Examples 2-7 were carried out according to the method of Example 1 with the modifications indicated below to produce various additional compounds of the present invention.

EXAMPLE 2

COMPOUND VII

7-[(Diisopropylamino)methylene]amino-$N^{10}$-(diisopropylamino)methylene-9a-methoxymitosane A suspension of mitomycin C (200 mg, 0.6 mM) in N,N-diisopropylformamide diethyl acetal (3 ml) was heated with stirring at 53° C. for 15 hours. The reaction mixture was poured into 50 ml of water and extracted with ethyl acetate (3×30 ml). The combined organic extract was dried (Na$_2$SO$_4$) and evaporated to yield a dark green syrup, tlc (methylene chloride/methanol 10:1) revealed a major green component at Rf=0.43 with faster moving (Rf=0.45–0.50) impurities. The major component VII was isolated as a dark green solid (156 mg, 46.8%) by two flash chromatography procedures using methylene chloride/methanol 20:1 as the eluting solvent.

NMR (CDCl$_3$, δ): 1.10–1.50 (5 singlets, 24H), 1.94 (s, 3H), 2.78 (dd, 1H, J=4, 2 Hz), 3.05 (d, 1H, J=4 Hz), 3.22 (s, 3H), 3.60 (m, 5H), 3.75 (dd, 1H, J=10, 4 Hz), 4.24 (d, 1H, J=12 Hz), 4.56 (t, 1H, J+10 Hz), 4.88 (dd, 1H, J=10, 4 Hz), 7.83 (s, 1H), 8.67 (s, 1H).

IR (KBr), $_{max}$, cm$^{-1}$: 3320, 2990, 2940, 1680, 1630, 1600, 1550, 1235, 1060.

UV(MeOH) λ$_{max}$, nm: 246 and 393.

Analysis: Calc'd for C$_{29}$H$_{44}$N$_6$O$_5$: C, 62.55; H, 7.91; N, 15.10. Found: C, 62.03; H, 7.80; N, 14.60.

EXAMPLE 3

COMPOUND XIV

7-[(Dimethylamino)methylene]amino-$N^{10}$-(dimethylamino)methylene-9a-methoxy-$N^{1a}$-methylmitosane In this example porfiromycin ($N^{1a}$-methyl mitomycin C), 130 mg, (0.37 mM) was substituted as a starting material in the reaction with 0.8 ml. (1.5 mM) of N,N-dimethyl formamide dimethyl acetal using 10 ml of chloroform and 2 ml of methanol as reaction solvent and a reaction period of 50 minutes at 50° C. Compound XIV was obtained as a syrup after evaporation of the reaction solvent; purified by flash chromatography using 20 g. of silical gel and methylene chloride/methanol (20:1) as the eluting solvent.

NMR (pyridine d$_5$, δ): 2.22 (bs, 4H), 2.28 (s, 3H), 2.70 (d, 1H, J=4 Hz), 2.80 (s, 3H), 2.84 (s, 3H), 2.90 (s, 6H), 3.20 (s, 3H), 3.52 (dd, 1H, J=2, 12 Hz), 4.10 (dd, 1H, J=4, 11 Hz), 4.38 (d, 1H, J=12 Hz), 4.92 (t, 1H, J=11 Hz), 4.96 (bs, 1H), 5.46 (dd, 1H, J=4, 11 Hz), 7.86 (s, 1H), 8.70 (s, 1H).

Rf=0.53, thin layer chromatography with 9:1 methylene chloride/methanol.

IR (KBr) ν$_{max}$, cm$^{-1}$: 2930, 1680, 1620, 1545, 1230, 1115.

UV(MeOH) λ$_{max}$, nm: 386 and 243.

Analysis: Calc'd for C$_{22}$H$_{30}$N$_6$O$_5$: C, 57.60; H, 6.55; N, 18.33. Found: C, 57.11; H, 6.11; N, 17.99.

This procedure produced Compound XV, 7-amino-$N^{10}$-dimethylaminomethylene-9a-methoxy-$N^{1a}$-methylmitosane, as a by-product in 30% yield, tlc Rf=0.40 (methylene chloride/methanol 9:1).

NMR (pyridine d$_5$, δ): 2.02 (s, 3H), 2.16 (dd, 1H, J=2, 5 Hz), 2.25 (s, 3H), 2.66 (d, 1H, J=5 Hz), 2.76 (s, 3H), 2.86 (s, 3H), 3.18 (s, 3H), 3.51 (dd, 1H, J=2, 12 Hz), 4.08 (dd, 1H, J=4, 10 Hz), 4.50 (d, 1H, J=10 Hz), 4.90 (t, 1H, J=10 Hz), 5.05 (bs), 5.43 (dd, 1H, J=4, 10 Hz), 8.70 (s, 1H).

IR (KBr) ν$_{max}$, cm$^{-}$: 3430, 3330, 3270, 2940, 2960, 1690, 1625, 1553, 1230, 1125.

UV(MeOH) λ$_{max}$, nm: 358, 244 and 216.

Analysis: Calc'd for C$_{19}$H$_{25}$N$_5$O$_5$: C, 56.53; H, 6.20; N, 17.38. Found: C, 54.68; H, 6.13; N, 16.59.

EXAMPLE 4

Compound IX

9a-Methoxy-7-[(1-piperidinylamino)methylene]amino-$N^{10}$-(1-piperidinylmethylene)mitosane N-(diethoxymethyl)piperidine, 3 ml, and mitomycin C, 200 mg, were allowed to react at 60° C. for 2.5 hours in chloroform (3 ml) solution. The product was obtained in 27.6% yield, tlc Rf=0.20 (methylene chloride/methanol 20:1).

NMR (pyridine d$_5$, δ): 1.38 (bs, 12H), 2.20 (s, 3H), 2.80 (bs, 1H), 3.24 (s, 3H), 3.00–3.40 (m, 5H), 3.40–3.80 (m, 5H), 4.13 (dd, 1H, J=10, 4 Hz), 4.45 (d, 1H, J=12 Hz), 4.90 (bs, 2H), 5.12 (t, 1H, J=10 Hz), 5.56 (dd, 1H, J=10 4 Hz), 7.87 (s, 1H), 8.70 (s, 1H).

IR (KBr) ν$_{max}$, cm$^{-}$: 3300, 2950, 2870, 1680, 1630, 1610, 1550, 1200, 1070.

UV(H$_2$O) λ$_{max}$, nm: 394 and 246.

Analysis: Calc'd for C$_{27}$H$_{36}$N$_6$O$_5$: C, 61.79; H, 6.87; N, 16.02. Found: C, 61.01; H, 6.85; N, 15.34.

The $N^{1a}$-formyl derivative of the foregoing substance, Compound VIII $N^{1a}$-formyl-9a-methoxy-7-[(1-piperidinylamino)methylene]amino-$N^{10}$-(1-piperidinylmethylene)mitosane was obtained as a major component, 43% yield, tlc Rf=0.25 (methylene chloride/methanol 20:1).

NMR (pyridine d$_5$, δ): 1.38 (bs, 12H), 2.23 (s, 3H), 3.00–3.40 (m, 4H), 3.23 (s, 3H), 3.40–3.90 (m, 6H), 4.07 (d, 1H, J=4 Hz), 4.18 (dd, 1H, J=11, 4 Hz), 4.63 (d, 1H), 4.90 (t, 1H, J=11 Hz), 4.94 (bs, 1H), 5.54 (dd, 1H, J=11, 4 Hz), 7.94 (s, 1H), 8.71 (s, 1H), 9.08 (s, 1H).

IR (KBr) ν$_{max}$, cm$^{-}$: 2490, 2860, 1698, 1630, 1600, 1540, 1250, 1060.

UV(H$_2$O) λ$_{max}$, nm: 394 and 247.

Analysis: Calc'd for C$_{28}$H$_{36}$N$_6$O$_6$: C, 60.08; H, 6.52; N, 15.21. Found: C, 59.99; H, 6.17; N, 15.07.

EXAMPLE 5

Compound X

9a-Methoxy-7-[(1-morpholino)methylene]amino-$N^{10}$-(1-morpholinomethylenemitosane A stirred suspension of mitomycin C (200 mg, 0.6 mM), in chloroform (10 ml) and N-diethoxymethyl morpholine (4 ml) was heated at approximately 53° C. for 42 hours. The reaction mixture was concentrated to a syrup under high vacuum. A crude flash chromatography (methylene chloride/methanol 25:1) separation was performed to isolate the green colored components from the excess of reagents. The combined green components were dissolved in 20 ml ethyl acetate, and washed with water (3×20 ml). The combined wash was reextracted with ethyl acetate (3×15 ml). All ethyl acetate fractions were combined, dried (Na$_2$SO$_4$) and evaporated to a dark green syrup, tlc (methylene chloride/methanol 10:1) of which revealed a distinct green component at Rf=0.33 with several green impurities (Rf 0.35–0.40). Upon flash chromatography the component at Rf 0.33 was isolated (130 mg, 56.8%) as a dark green amorphous solid which was characterized as Compound X.

NMR (CDCl$_3$, δ): 1.91 (s, 3H), 2.80 (bs, 1H), 3.13 (d, 1H, J=2 Hz), 3.22 (s, 3H), 3.30-3.94 (m, 18H), 4.20 (d, 1H, J=12 Hz), 4.40 (bs, 1H), 4.54 (t, 1H, J=10 Hz), 4.88 (dd, 1H, J=10 Hz, 4 Hz), 7.74 (s, 1H), 8.51 (s, 1H).

IR(KBr)$\nu_{max}$, cm$^{-1}$: 3300, 2970, 2920, 1680, 1625, 1550, 1235, 1070.

UV(MeOH)$\lambda_{max}$, nm: 386 and 244.

Analysis: Calc'd for C$_{25}$H$_{32}$N$_6$O$_7$: C, 56.78; H, 6.06; N, 1590. Found: C, 53.07; H, 6.03; N, 15.37.

EXAMPLE 6

Compound XVI

7-Amino-N$^{10}$-dimethylaminomethylene-9a-methoxymitosane

Mitomycin C, (200 mg, 0.6 mM) was dissolved in 10 ml. of chloroform and 2 ml. of methanol, N,N-dimethylformamide dimethyl acetal (0.64 ml, 4.8 mM) was added, and the solution was stirred at approximately 50° C. for 50 minutes. Thin layer chromatography (methylene chloride/methanol 90:10) revealed a trace amount of unreacted mitomycin C (Rf=0.22) and two new components (Rf=0.42, and 0.33 respectively). The solution was concentrated under reduced pressure to a syrup which was flash chromatographed (25 gm silica gel) using methylene chloride/methanol (20:1) as the eluting solvent.

The faster component (Rf=0.42) was isolated as a green amorphous solid (60 mg, 22.5%) and identified as Compound V by its NMR spectrum (pyridine d$_5$.

The major blue component (Rf=0.33) was isolated as an amorphous solid (148 mg, 63.3%) and characterized as Compound XVI. An analytical sample was obtained by precipitation from methylene chloride and n-pentane.

NMR (pyridine d$_5$, δ): 2.02 (s, 3H), 2.76 (bs, 4H), 2.86 (s, 3H), 3.21 (s, 3H), 3.28 (d, 1H, J=4 Hz), 3.62 (dd, 1H, J=2, 13 Hz), 3.94 (bs), 4.14 (dd, 1H, J=4, 12 Hz), 4.56 (d, 1H, J=13 Hz), 5.12 (t, 1H, J=10 Hz), 5.52 (dd, 1H, J=4, 10 Hz).

IR (KBr) $\nu_{max}$, cm$^{-1}$: 3430, 3320, 3280, 2930, 1675, 1615, 1650 1230, 1115.

UV(H$_2$O) $\lambda_{max}$, nm: 364, 244 and 219.

Analysis: Calc'd for C$_{18}$N$_{23}$N$_5$O$_5$: C, 55.48; H, 5.91; N, 17.98. Found: C, 54.70; H, 6.14; N, 17.95.

EXAMPLE 7

Compound XVII 7,9a-Dimethoxy-N$^{10}$-dimethylaminomethylenemitosane

Mitomycin A (170 mg) was substituted for mitomycin C of Example 1 and was allowed to react with N,N-dimethylformamide dimethylacetal (0.6 ml) in chloroform/methanol (10:1) solution at 50° C. for 1 hr. The desired product was obtained in 48% yield, tlc Rf=0.50 (methylene chloride/methanol 9:1).

NMR (pyridine d$_5$, δ): 1.83 (s, 3H), 2.76 (bs, 4H), 2.86 (s, 3H), 3.22 (s, 3H), 3.28 (d, 1H), 3.56 (dd, 1H, J=2, 13 Hz), 4.02 (s, 3H), 4.10 (dd, 1H, J=4, 10 Hz), 4.24 (d, J=13 Hz), 5.10 (t, 1H, J=10 Hz), 5.50 (dd, 1H, J=4, 10 Hz), 8.67 (s, 1H).

IR (KBr) $\nu_{max}$, cm$^{-1}$: 3300, 2930, 1675, 1655, 1625, 1500 1235, 1120.

UV (H$_2$O) $\lambda_{max}$, nm: 530, 316 and 244.

Analysis: Calc'd for C$_{19}$H$_{24}$N$_4$O$_6$: C, 56.39; H, 5.94; N, 13.85. Found: C, 56.61; H, 5.92; N, 13.71.

The N$^{1a}$-formyl derivative of Compound XVII was obtained as Compound XVIII, 7,9a-Dimethoxy-N$^{10}$-dimethylaminomethylene-N$^{1a}$-formylmitosane in 16.5% yield, tlc Rf=0.61 (methylene chloride/methanol 9:1).

NMR (pyridine d$_5$, δ): 1.88 (s, 3H), 2.76 (s, 3H), 2.85 (s, 3H), 3.54 (d, 1H), 3.62 (bs, 1H), 4.05 (s, 3H), 4.05 (bs, 1H), 4.14 (dd, 1H, J=4, 12 Hz), 4.40 (d, 1H, J=13 Hz), 4.86 (t, 1H, J=12 Hz), 5.42 (dd, 1H, J=4, 12 Hz), 8.66 (s, 1H), 9.08 (s, 1H).

EXAMPLE 8

Compound XIX 7-(Dimethylaminomethylene)amino-9a-methoxymitosane

To Compound V (600 mg, 1.35 mM) dissolved in methanol (10 ml) was added aminodiphenylmethane (2.2 ml, 10.8 mM) and the resulting solution was stirred at 54° C. for 4 hrs. The progress of the reaction was monitored by tlc (methylene chloride/methanol 90:10). At the end of 4 hrs. the starting material (Rf=0.35) had disappeared and a major new green zone (Rf=0.29) appeared instead. The solution was concentrated at reduced pressure and the resulting syrup was flash chromatographed (25 g silica gel) using methylene chloride/methanol 20:1 as the eluant. Fractions containing the green component (Rf=0.29) were pooled, dried (Na$_2$SO$_4$) and concentrated. Compound XIX was obtained as an amorphous solid (215 mg, 41%).

NMR (pyridine d$_5$, δ): 2.18 (s, 3H), 2.70 (bs, 1H), 2.80 (s, 3H), 2.88 (s, 3H), 3.08 (bs, 1H), 3.24 (s, 3H), 3.56 (bd, 1H, J=12 Hz), 4.00 (dd, 1H), 4.44 (d, 1H, J=12 Hz), 5.06 (t, 1H, J=10 Hz), 5.56 (dd, 1H, J=10, 4 Hz), 7.58 (bs, 2H), 7.88 (s, 1H).

IR (KBr) $\nu_{max}$, cm$^-$: 3300-3450, 2960-2910, 1715, 1620, 1535, 1050.

UV (H$_2$O) $\lambda_{max}$, nm: 390 and 226.

Anal. Calc'd for C$_{18}$H$_{23}$N$_5$O$_5$: C, 55.48; H, 5.91; N, 17.98. Found: C, 54.83; H, 5.67; N, 16.90.

When the N$^{1a}$-formyl derivative, Compound VI, was substituted as starting material for Compound V in Example 8, but using room temperature for 20 hrs. as reaction conditions, Compound XIX was produced in substantially the same fashion and yield.

EXAMPLE 9

Compound XX 7-(Dimethylaminomethylene)aminio-9a-methoxy-N$^{1a}$-methylmitosane

Compound XIV, 1 g, (2.18 mM), was dissolved in methanol (20 ml), aminodiphenylmethane (3.5 ml, 17.18 mM) was added, and the resulting solution was stirred at room temperature for 5 hours and at 40° C. for 5 hours. Thin layer chromatography (CH$_2$Cl$_2$/MeOH 90:10) of the reaction mixture revealed that almost all of the starting material (Rf=0.55) had been consumed and a major new green zone (Rf=0.48) had appeared. Workup similar to that described in Example 8 afforded Compound XX as an amorphous solid (350 mg). Further purification was accomplished by flash chromatography (7 g, silica gel) using CH$_2$Cl$_2$/MeOH (250 ml, 96/4 v/v) and precipitation of the resulting solid (Rf=0.48) from methylene chloride (5 ml) and hexane (50 ml) to afford analytically pure XX (314 mg, 35.7%) as a solid.

NMR (CDCl$_3$, δ): 1.93, s, 3H), 2.26 (bs, 1H), 2.26 (s, 3H), 3.06 (s, 3H), 3.08 (bs, 1H), 3.10 (s, 3H), 3.20 (s, 3H), 3.46 (bd, 1H, J=12, 1 Hz), 3.58 (dd, 1H, J=4, 10 Hz), 4.17 (d, 1H, J=12 Hz), 4.38 (t, 1H, J=10 Hz), 4.68 (m, 2H), 4.76 (dd, 1H, J=4, 10 Hz), 7.72 (s, 1H).

IR (KBr) $\nu_{max}$, cm$^{-1}$: 3440, 3350, 3190, 3020, 2940, 2910, 1725, 1630, 1550, 1055.

UV (MeOH) $\lambda$max, nm: 386 and 231.

Analysis: Calc'd for $C_{19}H_{25}N_5O_5$: C, 56.53; H, 6.20; N, 17.36. Found: C, 53.90; H, 5.13; N, 15.81.

EXAMPLE 10

Compound XI 7-(n-Propyl)amino-9a-methoxymitosane

Compound V (330 mg, 0.74 mM) was dissolved in anhydrous methanol (10 ml), and n-propylamine (1.0 ml) was added to it. The reaction mixture was stirred for 6 hrs. at room temperature and for 16 hrs. at about 0°–4°. The solvent and excess reagent were evaporated under reduced pressure and the residue was flash chromatographed using silica gel as adsorbent. The blue component (Rf=0.40) obtained by elution with methylene chloride/methanol 30:1 was reprecipitated from methylene chloride with hexane to yield Compound XI as an amorphous grey powder (125 mg, 44.5%).

NMR (pyridine d$_5$, δ): 0.80 (t, 3H), 1.42 (m, 2H), 2.11 (s, 3H), 2.74 (bs, 1H), 3.12 (bs, 1H), 3.22 (s, 3H), 3.36 (q, 2H), 3.60 (d, 1H, J=12 Hz), 3.96 (dd, 1H, J=11 Hz), 4.54 (d, 1H, J=12 Hz), 5.00 (m, 3H), 5.36 (dd, 1H, J=11, 4 Hz), 6.90 (t, 1H).

IR(KBr) $\nu_{max}$, cm$^{-1}$: 3440, 3300, 2960, 2940, 1715, 1630, 1600, 1550, 1510, 1220, 1060.

UV(H$_2$O) $\lambda_{max}$, nm: 372 and 222.

Analysis: Calc'd for $C_{18}H_{24}N_4O_5$: C, 57.40; H, 6.38; N, 14.88. Found: C, 57.28; H, 6.41; N, 14.08.

EXAMPLE 11

Compound XII 7-(2-Hydroxyethyl)amino-9a-methoxymitosane

Compound V (330 mg, 0.74 mM) was dissolved in anhydrous methanol (5 ml) ethanolamine (2 ml) was added. The reaction mixture was stirred at room temperature for 2 hrs., and then diluted with water (50 ml) and extracted with ethyl acetate (5×60 ml). The combined ethyl acetate extracts were dried (Na$_2$SO$_4$) and concentrated to a bluish-purple residue, which upon column chromatography using 10% methanol in methylene chloride and concentrating the pooled fractions containing the blue compound, afforded 105 mg (37%) of Compound XII as an amorphous solid.

NMR (pyridine d$_5$, δ): 2.14 (s, 3H), 2.81 (bs, 1H), 3.18 (d, 1H, J=4 Hz), 3.24 (s, 3H), 3.65 (dd, 1H, J=2, 12 Hz), 3.70–4.20 (m, 5H), 4.52 (d, 1H, J=13 Hz), 4.96 (t, 1H, J=12 Hz), 7.38 (t, 1H), 7.58 (bs).

IR(KBr) $\nu_{max}$, cm$^{-1}$: 3300–3500, 2930, 1710, 1630, 1600, 1540, 1510, 1200, 1055.

UV(H$_2$O) $\lambda_{max}$, nm: 371 and 221.

Analysis: Calc'd for $C_{17}H_{22}N_4O_6$: C, 53.92; H, 5.82; N, 14.80. Found: C, 51.30, H, 5.88; N, 14.80.

EXAMPLE 12

Compound XIII

7-[2-Benzylthioethyl]amino-9a-methoxymitosane

Compound V (200 mg, 0.45 mM) was dissolved in methanol (2 ml), S-benzyl 2-aminoethanethiol (0.5 ml) was added and the solution was stirred at room temperature for 16 hrs. The residue obtained upon evaporation of the solvent at reduced pressure was flash chromatographed (40 gm, silica gel) using 6% methanol/methylene chloride (400 ml) as the eluant. The blue component (Rf approximately 0.5 in 10% MeOH/CH$_2$Cl$_2$) was isolated as an amorphous solid (65 mg, 29.8%). Its spectral data (NMR, IR, UV and mass spec.) were in agreement with the assigned structure.

Analysis: Calc'd for $C_{24}H_{28}N_4O_5S$: C, 59.49; H, 5.82; N, 11.56. Found: C, 59.72; H, 5.94; N, 11.08.

EXAMPLE 13

Preparation of

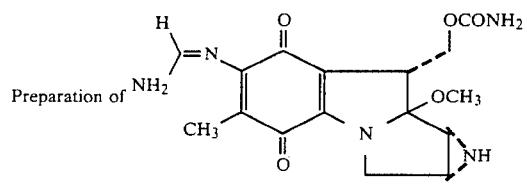

(A) To a solution of isopropylformimidate hydrochloride (1 mmol) in dimethylformamide (DMF), 2 ml, is slowly added diisopropylethylamine (2.1 mmol) at 0° C. under a nitrogen atmosphere. To the resulting solution is added dropwise β-trimethylsilylethyl chloroformate at 0° C. The resulting clear solution is designated solution A.

(B) A solution of mitomycin C (1 mmol) in 5 ml. of DMF is added to a suspension of sodium hydride (1.5 mmol) in 3 ml of DMF. The solution is stirred at room temperature for 20 minutes and cooled to −40°~−50° C., before addition of solution A (above). The solution is kept at −40° C. for 1 hour and then allowed to warm up to room temperature. After standing at room temperature for approximately 6–18 hours, the reaction mixture is diluted with CH$_2$Cl$_2$ and filtered. The solid residue obtained after evaporation of the filtrate is chromatographed on silica gel to isolate the amidino protected title compound.

(C) The amidino protecting group of the preceding intermediate is removed by the published procedure of Carpino and Tsao (J. Chem. Soc. Chem. Comm. 358 (1978)) to yield unsubstituted amidino title compound.

EXAMPLE 14

Preparation of

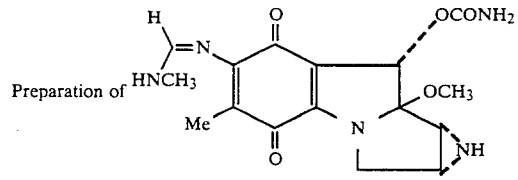

(A) To a solution of isopropylformimidate hydrochloride (1 mmol) in DMF (2 ml) is slowly added diisopropylethylamine (21 mmol) at 0° C. under a nitrogen atmosphere. To the resulting solution is added methyliodide at 0° C. The resulting solution is designated solution B.

(B) The procedure outlined in Example 13(B) is repeated with substitution of solution B for solution A to obtain the title compound.

EXAMPLE 15

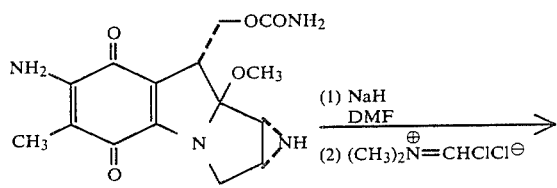

Mitomycin C

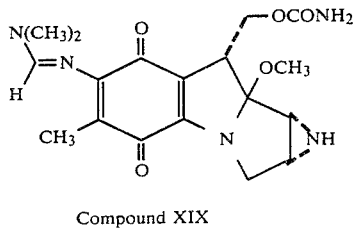

Compound XIX

A 0.5 M solution of N,N-dimethylchloromethyleniminium chloride was prepared by dropwise addition of oxalyl chloride (1.57 g. 12.5 mmol) at 0° C. to a solution of DMF (915 mg. 12.5 mmol) in 25 ml of CHCl₃ followed by stirring at room temperature for 30 minutes. Separately, a solution of mitomycin C (334 mg, 1 mmol) in 5 ml of DMF was added to a suspension of NaH (36 mg, 1.5 mmol) in 3 ml of DMF. The solution was stirred at room temperature for 20 minutes and cooled to −40° ~ −50° C. and the above solution of N,N-dimethylchloromethyleniminium chloride (3 ml, 1.5 mmol) was then added. Additional NaH (18 mg, 0.75 mmol) was added after 10 minutes of stirring at −40° C. The solution was kept at −40° C. for 1 hour and then diluted with CH₂Cl₂ and filtered. The residue obtained after evaporation of the filtrate was chromatographed by thin layer chromatography (TLC) on silica gel (10% CH₃OH—CH₂Cl as elutant). Extraction of the major green band yielded 78 mg (43% based on the recovered mitomycin C) of an amorphous solid whose NMR spectrum and TLC behavior were identical to those of Compound XIX prepared in Example 8. Extraction of the purple band gave 150 mg of mitomycin C.

EXAMPLE 16

7(1-Methyl-2-(H)-pyridinylidene)amino-9a-methoxymitosane

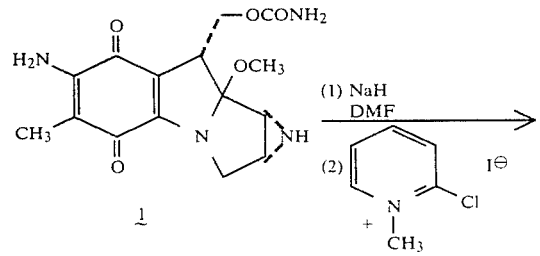

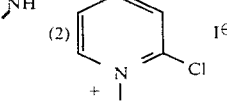

-continued

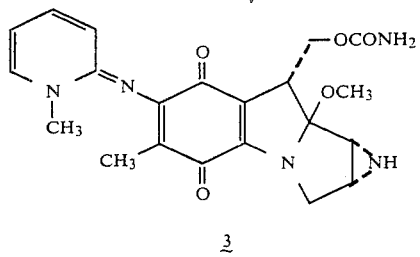

To a mixture of mitomycin C (242 mg, 0.725 mmol) and NaH (43.5 mg, 1.81 mmol) there was added 4 ml of DMF. After stirring 15 minutes, 2-chloro-1-methyl-pyridinium iodide (370 mg, 1.45 mmol) was added to room temperature. The solution was stirred for 1.5 hour and then diluted with etyl acetate (EtOAc) and filtered. The residue obtained after evaporation of the filtrate was chromatographed (TLC) on silica gel (5% CH₃OH—CH₂Cl₂ as a elutant). The minor product (12 mg) was Compound XIX (Example 8). The major product (75 mg) was further purified by silica gel TLC (10% CH₃OH—CH₂Cl₂) to give 6 mg (2%) of the title compound: NMR (pyridine d₅, δ) 2.11 (s, 3H), 2.76 (bs, 1H), 3.20 (m, 1H), 3.26 (s, 3H), 3.49 (s, 3H), 3.63 (dd, 1H, J=13, 1 Hz), 4.01 (dd, 1H, J=11, 4 Hz), 4.51 (d, 1H, J=13 Hz), 5.10 (t, 1H, J=10 Hz), 5.43 (dd, 1H, J=10, 4 Hz), 5.99 (dt, 1H, J=9, 2 Hz), 6.09 (dd, 1H, J=9, 1 Hz), 6.95 (dd, 1H, J=7, 2 Hz), 7.32 (dd, 1H, J=7, 1 Hz).

EXAMPLE 17

7-[(Methylaminomethylene)amino]-9a-methoxymitosane

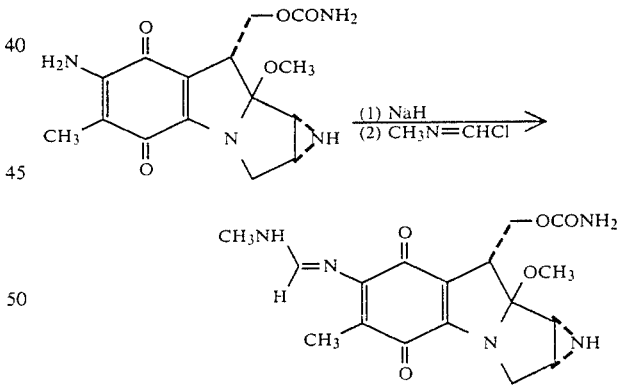

Sodium hydride (12 mg, 0.5 mmol) is added under a nitrogen atmosphere to a solution of mitomycin C (167 mg, 0.5 mmol) in 2 ml of hexamethylphosphoramide. To this solution is added N-methylformimidoyl chloride (19 mg. 0.25 mmol, N. H. Bosshard and H. Zollinger, Helv. Chim. Acta, 42, 1659 (1959). The solution is stirred at room temperature for 10 minutes and then NaH (6 mg, 0.25 mmol) and N-methylformimidoyl chloride (9.5 mg, 0.13 mmol) are added. After stirring for 6–12 hours the solution is diluted with ethyl acetate and filtered. Evaporation of the solvent followed by a chromatographic purifiction of the residue gives the title compound.

EXAMPLE 18

Compound XXI

9a-Methoxy-7-(1-morpholinomethylene)aminomitosane

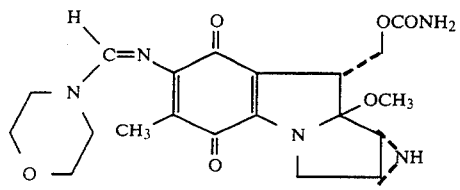

To mitomycin C (600 mg, 1.8 mM) suspended in chloroform (30 ml) was added 4-diethoxymethyl morpholine (12.5 ml) and the resulting suspension heated at 58° C. for 48 hours. At the end of 48 hours TLC (20% MeOH in CH$_2$Cl$_2$) revealed that the reaction was incomplete. The solution was concentrated under reduced pressure, and to the resulting syrup was added water (100 ml). After stirring for 20 minutes the dark green solution was extracted with methylene chloride (5x50 ml), and the combined extract was dried and concentrated to a syrup. To this syrup, in methanol (20 ml), was added aminodiphenylmethane (6.5 ml), and the resulting solution was stirred at 30°-35° C. for 18 hours. Thin layer chromatography (20% MeOH in CH$_2$Cl$_2$) revealed one major green zone with a minor slower purple zone. The solution was concentrated under reduced pressure, and the resulting syrup was purified by the usual flash chromatography technique to obtain the title compound as a dark green amorphous solid (75 mg, 10%). Analytical sample was obtained by precipitating it out from a methylene chloride solution with n-hexane.

NMR (pyridine d$_5$, δ):216 (s, 3H), 2.76 (dd, 1H, J=5 and 1Hz), 3.16 (d, 1H, J=5 Hz), 3,24 (s, 3H), 3.28–3.80 (m, 10H), 4.02 (dd, 1H, J=10 and 4Hz), 4.40 (d, 1H, J=12Hz), 5.06 (t, 1H, J=10 Hz), 5.46 (dd, 1H, J=10 and 4 Hz), 7.90 (s, 1 H).

IR(KBr) $\nu_{max}$ cm$^{-1}$: 3360, 3280, 2960, 2920, 1720, 1600, 1520, 1230, 1050.

UV(MeOH) $\lambda_{max}$: 384 and 234.

Anal. Calc'd for C$_{20}$H$_{25}$N$_5$O$_6$: C, 55.64; H, 5.80; N, 16.23. Found: C, 55.07; H, 5.55; N, 15.88.

EXAMPLE 19

Compound XXII 7-(1-Pyrrolidinylmethylene)amino-9a-methoxymitosane

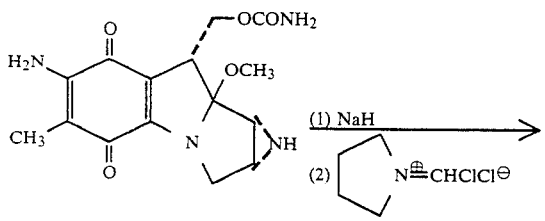

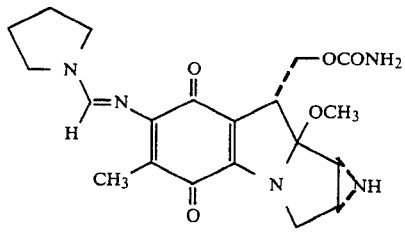

A 0.5 molar solution of pyrrolidinylchloromethyleniminium chloride was prepared by dropwise addition of oxalyl chloride (3.17 g, 25 mmol) at 0° C. to a solution of 1-formylpyrrolidine (2.48 g, 25 mmol) in 50 ml of CHCl$_3$ followed by stirring at room temperature for 30 minutes. Separately, sodium hydride (24 mg, 1 mmol) was added under nitrogen atmosphere to a solution of mitomycin C (334 mg, 1 mmol) in 3 ml of 1-formylpyrrolidine. After 20 minutes of stirring at room temperature, the solution was cooled to −40° ∼ −50° C., and the iminium salt solution prepared above (1 ml, 0.5 mmol) was added. To this mixture was added alternately, at 10 minute intervals, 12 mg (0.5 mmol) of NaH, 0.5 ml (0.25 mmol) of the iminium salt solution, 6 mg (0.25 mmol) of NaH, 0.25 ml (0.125 mmol) of the iminium salt solution, and finally 3 mg (0.125 mmol) of NaH, and 0.125 ml (0.063 mmol) of the iminium salt solution. After 30 minutes of stirring at −30° C. the mixture was warmed up to room temperature. It was diluted with ethyl acetate and the inorganic salt was filtered off. The residue obtained after evaporation of the solvent was chromatographed by thin layer chromatography on silica gel (10% CH$_3$OH—CH$_2$Cl$_2$). Extraction of the green band gave 120 mg (15% yield) of the title compound:

NMR (pyridine d$_5$, δ) 1.58 (m, 4 H), 2.29 (s, 3 H), 2.73 (m, 1 H), 3.06-3.50 (m, 8 H), 3.59 (dd, 1 H, J=13, 1 Hz), 4.03 (dd, 1 H, J=10, 4 Hz), 4.44 (d, 1 H, J=12 Hz), 5.05 (t, 1 H, J=10 Hz), 5.45 (dd, 1 H, J=10, 4 Hz), 8.04 (s, 1 H)

IR (KBr) $\nu_{max}$, cm$^{-1}$: 3420, 3280, 2960–2870, 1715, 1625, 1560, 1300, 1055.

EXAMPLE 20

7-[N-Methyl-N-(methylamino)methyl]amino-9a-methoxymitosane

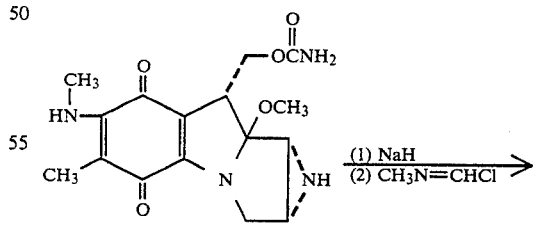

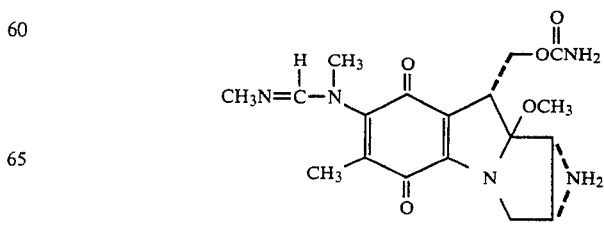

The procedure of Example 17 is repeated with substitution of 9a-methoxy-7-(N-methylamino)mitosane (Matsui et al., The Journal of Antibiotics, XXI, 189–198 (1968)) for mitomycin C in like molecular amount.

EXAMPLE 21

Compound XXIII
7-[1-(Dimethylamino)ethylidene]amino-$N^{10}$-[1-(dimethylamino)ethylidene]-9 -methoxymitosane

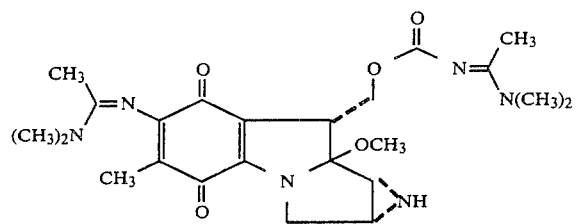

A suspension of 600 mg. (1.79 mM) of mitomycin C in 2 ml of methanol was prepared and treated with 3 ml of N,N-dimethylacetamide dimethylacetal. The suspension was heated at 75°–80° C. with stirring for 2 hrs. At this stage TLC ($CH_2Cl_2$/methanol 10:1) revealed that nearly all of the mitomycin C have been consumed by the reaction. The product appeared as a green zone. The solvent and volatile materials were removed by concentrating the reaction mixture to dryness at reduced pressure yielding a syrup which was dissolved in methylene chloride and loaded onto a silica gel column (40 g silica gel), and the column was developed with 1% methanol in methylene chloride (200 ml), 2% methanol in methylene chloride (200 ml), and 5% methanol in methylene chloride (400 ml). The fractions containing the green zone representing the product were combined and concentrated to an amorphous solid weighing 110 mg (13% yield). This material was dissolved in 2 ml of acetone and precipitated from the solution by the addition of hexane. The product was collected by filtration.

Anal. Calc'd for $C_{23}H_{32}N_6O_5$: C, 58.46; H, 6.83; N, 17.79. Found: C, 58.89; H, 6.89; N, 17.64.

UV (MeOH) λmax. nm: 235, 364.

IR (KBr) $\nu_{max}$, $cm^{-1}$: 3440, 3295, 2925, 1770, 1660, 1620, 1580, 1550, 1300, 1055.

The $^1H$ N.M.R. spectrum in pyridine $d_5$ is consistent with the structure of the title compound.

EXAMPLE 22

Compound XXIV
7-[1-(Dimethylamino)ethylideneamino]-9a-methoxymitosane

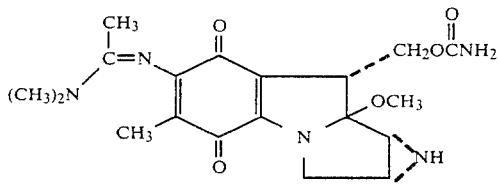

A solution of 100 mg. (0.21 mM) of Compound XXIII in 2 ml of chloroform was added to 2 ml of aminodiphenylmethane and the solution was heated at about 55°–60° C. for hrs. At this stage trace amounts of Compound XXIII remained in the reaction mixture, but it was, nevertheless, concentrated and the residue chromatographed over neutral alumina using gradient elution commencing with methylene chloride and concluding with methanol/methylene chloride 2.5:1. The major green zone was isolated as an amorphous green solid weighing 25 mg (29.4% yield). This material was purified by dissolving in acetone and adding hexane to the acetone solution until precipitation occurred. The product was collected by filtration and dried.

Anal. Calc'd for $C_{25}H_{32}N_6O_5$: C, 56.58; H, 6.20; N, 17.37. Found: C, 55.71; H, 6.34; N, 15.23.

UV ($H_2O$) λmax. nm: 374, 230 (shoulder)

IR (KBr)$\nu_{max}$, $cm^{-1}$: 3420, 3350, 3280, 2920, 1710, 1610, 1540, 1300, 1050.

The $^1H$ N.M.R. spectrum in pyridine $d_5$ is consistent with the structure.

EXAMPLE 23

Compound XXV
7-[(1-Methyl-2-pyrrolidinylidene)amino]-$N^{10}$-[(1-methyl-2-pyrrolidinylidene)amino]-9a-methoxymitosane

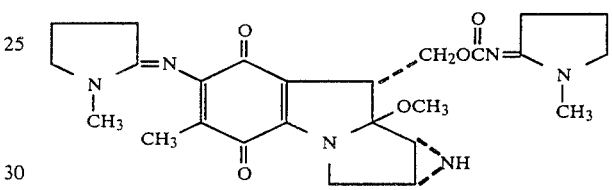

2,2-Dimethoxy-1-methylpyrrolidine (H. Eilingsfeld et al. Angew. Chem., 72, 836 (1960)), 1.5 g (10.3 mM) and 280 mg of mitomycin C (0.34 mM) in 20 ml of methanol were heated at 55° for five hours. The reaction mixture was examined by thin layer chromatography on an alumina plate using methylene chloride/methanol 97:3 as solvent. TLC revealed a major green spot representing the product and a minor blue spot representing mitomycin C starting material. The solvent was removed by distillation in vacuo at 40° C. and the residue was dissolved in methylene chloride and loaded onto a 4.5 cm column containing 150 g of alumina. Elution was with 50 ml of methylene chloride followed by 600 ml of 1% methanol in methylene chloride. Gross impurities were removed, but no pure fractions were isolated. The combined eluate was concentrated by distillation at 20° C. to an oily residue which apparently contained some of 2,2-dimethoxy-1-methylpyrrolidine. This material was again chromatographed on an alumina column (25 g of alumina) using 200 ml of methylene chloride followed by 100 ml of 1% methanol in methylene chloride. This resulted in removal of the 2,2-dimethoxy-1-methylpyrrolidine and resulted in a number of fractions containing minor impurities and several pure fractions confirmed by TLC (one green spot) representing the desired product, yield 53 mg.

Anal. Calc'd for $C_{25}H_{32}N_6O_5 \cdot 0.85 H_2O$: C, 58.66; H, 6.64; N, 16.42. Found: C, 58.63; H, 6.46; N, 16.50.

UV (MeOH) λmax. nm: 354, 239.

IR (KBr)$\nu_{max}$, $cm^{-1}$: 3300, 3220, 2940, 1660, 1620, 1550, 1290, 1055.

The $^1H$ N.M.R. spectrum in pyridine $d_5$ is consistent with the structure of the title compound.

EXAMPLE 24

7-[(1-Methyl-2-pyrrolidinylidene)amino]-9a-methoxymitosane

A solution of 80 mg (0.16 mM) of Compound XXV and 0.48 ml of n-butylamine in 15 ml of chloroform was heated at reflux for 48 hrs. TLC (methanol/methylene chloride, 2% on alumina) revealed a major green spot and a small leading blue spot and a small trailing red spot all trailing the starting material. The reaction solution was loaded onto a column containing 50 g of alumina and eluted with 200 ml of 1% methanol in methylene chloride followed by 400 ml of 2% methanol in methylene chloride. Those fractions containing a single major green component as revealed by TLC were combined and concentrated to a residue of the desired product weighing 24 mg.

NMR (pyridine $d_5$, δ): 1.72 (q, 2 H), 2.04 (s, 3 H), 2.16 (q, 2 H), 2.72 (bs, 1 H), 2.84 (s, 3 H), 3.12 (m, 3 H), 3.24 (s, 3 H), 3.60 (dd, 1 H, J=14, 2 Hz), 4.00 (dd, 1 H, J=12, 6 Hz), 4.40 (d, 1 H, J=14 Hz), 5.04 (t, 1 H, J=14 Hz), 5.38 (dd, 1 H, J=12, 6 Hz), 7.48 (bs, 2 H).

EXAMPLE 25

Compound XXVI
7-[(Methoxyamino)methylene]amino-9a-methoxymitosane

A solution of Compound XIX, 660 mg (1.7 mM), in 10 ml of methanol was prepared, and 170 mg (2.0 mM) of methoxyamine hydrochloride was added thereto. The solution was stirred at 10° C. for 3 hrs. and at room temperature for 2 hrs. TLC revealed only a trace of unreacted Compound XIX. A black precipitate formed on standing which was collected and washed with acetone, yield of desired product 380 mg (57%).

Anal. Calc'd for $C_{17}H_{21}N_5O_6$: C, 52.19; H, 5.40; N, 17.90. Found: C, 51.64; H, 5.40; N, 17.83.

UV (MeOH) λmax. nm: 376, 242.

IR (KBr)$v_{max}$, cm$^{-1}$: 3440, 3250, 3140, 2920, 1730, 1645, 1615, 1560, 1450, 1320, 1050.

The $^1$H N.M.R. spectrum in pyridine $d_5$ is consistent with the structure of either the title compound or its tautomer at C-7 i.e.

EXAMPLE 26

Compound XXVII
7-[(Benzyloxyamino)methylene]amino-9a-methoxymitosane

A solution of Compound XIX, 100 mg (0.26 mM), in 2 ml of methanol containing 0.5 ml of triethylamine was prepared and 400 mg (2.5 mM) of O-benzylhydroxylamine hydrochloride was added thereto. The reaction was allowed to proceed for 2.5 hrs. at room temperature. TLC (CH$_2$Cl$_2$/methanol 10:1) revealed a major orange-brown zone in advance of the green zone, the latter corresponding to Compound XIX. The reaction mixture was concentrated to a residue which was flash chromatographed over silica gel (20 g) using CH$_2$Cl$_2$/methanol 20:1 as the eluting solvent. The major brown zone constituting the desired product was collected as an amorphous solid weighing 80 mg (65.6% yield).

Anal. Calc'd for $C_{23}H_{25}N_5O_6$: C, 59.10; H, 5.35; N, 14.97. Found: C, 58.43; H, 5.48; N, 14.62.

UV (MeOH) λmax. nm: 376, 245, 209.

IR (KBr) $v_{max}$, cm$^{-1}$: 3460, 3300, 2945, 2920, 1745, 1720, 1570, 1275, 1220, 1060.

The $^1$H N.M.R. spectrum in pyridine $d_5$ is consistent with the structure of either the title compound or its tautomer at C-7 i.e.

Unreacted starting material, Compound XIX, weighing 10 mg was recovered.

EXAMPLE 27

Compound XXVIII
7-(1,3-Dimethyl-2-imidazolinylidene)-9a-methoxymitosane

Mitomycin C, 0.34 g (1 mmol) is dissolved in 5 ml of 1,3-dimethyl-2-imizadolidone and 0.1 g of sodium hydride (50% in oil, 2.08 mmol) is added thereto at room temperature. The mixture is kept at room temperature for 20 minutes, and then chilled in an ice salt bath (−15° C.). The mixture is kept for 10 minutes at this temperature and then 0.65 g (2 mmol) of 2-chloro-1,3-dimethyl-4,5-dihydro-(3H)-imidazoliminium chloride is taken thereto. It is kept at −15° C. for 1 hr. and then diluted with ethyl acetate and chromatographed on an alumina column. The column is eluted with methylene chloride followed by methylene chloride containing 2% v/v methanol. A green colored fraction is obtained consisting of the desired product which is further purified by chromatography on alumina using methylene chloride containing 10% v/v methanol, yield 20 mg (5%).

Anal. Calc'd for $C_{20}H_{26}N_6O_5 \cdot 1\frac{1}{4} H_2O$: C, 53.03; H, 6.34; N, 18.55. Found: C, 52.68; H, 6.21; N, 18.15.

NMR (pyridine-$d_5$, δ): 2.32 (s, 3H), 2.47 (s, 3H), 2.59 (s, 3H), 2.74 (m, 1H), 3.03–3.32 (m, 5H), 3.26 (s, 3H), 3.66 (bd, 1H, J=12 Hz), 4.02 (dd, 1H, J=11, 4 Hz), 4.75 (d, 1H, J=12Hz), 5.09 (bt, 1H, J=11 Hz), 5.44 (dd, 1H, J=11, 4 Hz).

IR (KBr): 3400, 3280, 2930, 1700, 1610, 1480, 1330, 1055 cm$^{-1}$.

UV (MeOH, λmax): 600, 375, 252 (sh), 222 nm.

EXAMPLE 28

Compound XXIX

7-[(1,3-Dimethyltetrahydropyrimidinylidene)amino]-9a-methoxymitosane

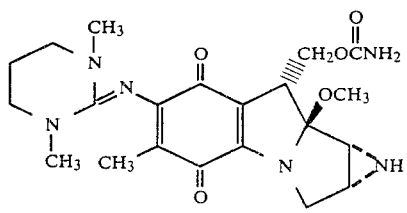

Sodium hydride (50% oil dispersion, 200 mg, 4.2 mmol) was added under nitrogen to a solution of mitomycin C (680 mg, 2 mmol) in 8 ml of 1,3-dimethyl-3,4,5,6-tetrahydro(1H,3H)-2-pyrimidinone. The mixture is kept for 20 minutes at room temperature and then cooled to −25° C. 2-Chloro-1,3-dimethyl-2,3,4,5-tetrahydro-pyrimidinium chloride, 0.73 g (4 mmol) is added thereto, and the mixture is then kept at −25° C. for 3 hrs. It is then diluted with ethyl acetate and 2 ml of methanol. The mixture without further treatment is loaded onto a dry alumina chromatographic column and eluted first with methylene chloride and then 2% v/v methanol/methylene chloride to yield the desired product 0.35 g (39.5% yield), m.p. 138°–140° C.

Anal. Calc'd for $C_{21}H_{27}N_6O_5 \cdot H_2O$: C, 54.65; H, 6.33; N, 18.21. Found: C, 54.78; H, 6.18; N, 18.21.

NMR (pyridine-$d_5$, δ) 1.80 (m, 2H), 2.42 (s, 3H), 2.52 (s, 3H), 2.64 (s, 3H), 2.76 (m, 1H), 2.90–3.30 (m, 5H), 3.26 (s, 3H), 3.74 (d, 1H, J=12 Hz), 4.05 (dd, 1H, J=11, 4 Hz), 4.97 (d, 1H, J=12 Hz), 5.09 (t, 1H, J=11 Hz), 5.41 (dd, 1H, J=11, 4 Hz).

IR (KBr): 3430, 3280, 2930, 1710, 1570, 1480, 1450, 1350, 1050 cm$^{-1}$.

UV (MeOH, λmax): 635, 377, 264 (sh), 223 nm.

EXAMPLE 29

Compound XXX 7-(Tetramethyldiaminomethylene)amino-9a-methoxymitosane

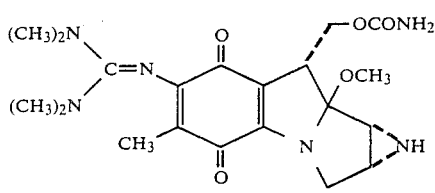

Mitomycin C, 425 mg (1.42 mmol), is mixed with a 50% dispersion in oil of sodium hydride, 85.3 mg, and 4 ml of dimethylformamide is added thereto. The mixture is stirred at room temperature under an atmosphere of argon for 10 minutes, and then cooled to −35° C. Tetramethylchloroformamidimium chloride, 289 mg (2.13 mmol), is added and the mixture is allowed to warm to 5° C. during a 2 hr. period. Crushed dry ice is then added to the mixture to quench the reaction, and the solvent is removed by distillation under reduced pressure. The residue is chromatographed on an alumina column (100 g) employing 3% v/v methanol in methylene chloride for elution. This material is further purified by alumina TLC (5% v/v methanol in methylene chloride) to yield two fractions of 17 mg and 76 mg. The latter is crystallized from acetone-ether to yield the desired product, m.p. 193°–195° C., (12% yield).

Anal. Calc'd for $C_{20}H_{28}N_6O_5$: C, 55.54; H, 6.53; N, 19.43. Found: C, 54.92; H, 6.53; N, 19.29.

NMR (pyrimidine-$d_5$, δ): 2.26 (s, 3H), 2.59 (s, 6H), 2.68 (s, 6H), 2.75 (m, 1H), 3.15 (d, 1H), J=4 Hz), 3.26 (s, 3H), 3.65 (d, 1H, J=12 Hz), 4.00 (dd, 1H, J=11, 5 Hz), 4.62 (d, 1H, J=12 Hz), 5.04 (t, 1H, J=11 Hz), 4.38 (dd, 1H, J=11, 5 Hz).

IR (KBr): 3430, 3280, 2920, 1710, 1610, 1495, 1335, 1055 cm$^{-1}$.

UV (MeOH, λmax): 610, 380, 260, 220 nm.

EXAMPLE 30

Compound XXXI 7-(1-Piperidinylmethylene)amino-9a-methoxymitosane

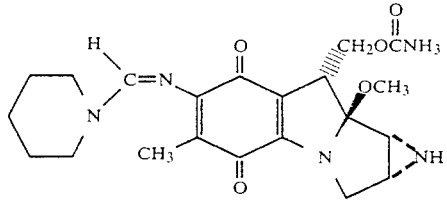

A 0.5 M solution of piperidinylchloromethyleniminium chloride is prepared by dropwise addition of oxalyl chloride (380 mg, 3 mmol) to 6 ml of chloroform containing 0.34 g, (3 mmol) of 1-formylpiperidine. Separately, sodium hydride (50% oil dispersion, 96 mg, 2 mmol) is added under nitrogen to a solution of mitomycin C (334 mg, 1 mmol) in 3 ml of 1-formylpiperidine. After 15 minutes of stirring at room temperature, the solution is cooled to −25° C. and the iminium salt solution prepared above (4 ml, 2 mmol) is added. The reaction mixture is kept at −25° C. for 1 hr. and quenched by addition of dry ice. After addition of methanol (1 ml), the product mixture is absorbed on neutral alumina. This material is placed on an alumina column (30 g). The column is eluted first with methylene chloride and then with 3% v/v methanol in methylene chloride to give 360 mg (84%) of the title compound, m.p. 68°–70° C.

Anal. Calc'd for $C_{21}H_{25}N_5O_6 \cdot 1\frac{1}{4}$ $H_2O$: C, 55.80; H, 6.58; N, 15.49. Found: C, 55.57; H, 6.21; N, 15.91.

NMR (pyridine-$d_5$, δ) 1.42 (bs, 6H), 2.19 (s, 3H), 2.72 (m, 1H), 3.06–3.30 (m, 3H), 3.25 (s, 3H), 3.48–3.70 (m, 2H), 3.57 (d, 1H, J=13 Hz), 4.01 (dd, 1H, J=11, 4 Hz). 4.43 (d, 1H, J=13 Hz), 5.02 (bt, 1H, 3=11 Hz), 5.55 (dd, 1H, J=11, 4 Hz), 7.86 (s, 1H).

IR (KBr) 3440, 3350, 3300, 2935, 2835, 1710, 1615, 1520, 1445, 1305, 1250, 1200, 1055 cm$^{-1}$.

UV (MeOH, λmax) 590, 389, 262 (sh), 234, 212 (sh) nm.

EXAMPLE 31

7-Hydroxy-$N^{10}$-dimethylaminomethylene-9a-methoxymitosane

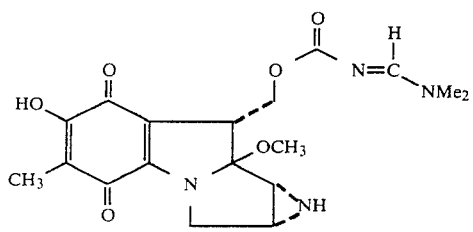

To a solution of 7-hydroxy-9a-methoxymitosane, (20 mg) in methylene chloride (3 ml) there is added dimethylformamide dimethylacetal (1 ml) and the solution is stirred at about 65° C. for 30 minutes. The progress of the reaction is followed by TLC (10:1 $CH_2Cl_2$/MeOH). The product is recovered by concentrating the mixture under reduced pressure and the residue is chromatographed over silica gel to yield the title compound.

Activity Against P-388 Murine Leukemia

Table IV contains the results of laboratory tests with $CDF_1$ female mice implanted intraperitoneally with a tumor inoculum of $10^6$ ascites cells of P-388 murine leukemia and treated with various doses of either a test compound of formula I or mitomycin C. The compounds were administered by intraperitoneal injection. Groups of six mice were used for each dosage level and they were treated with a single dose of the compound on day one only. A group of ten saline treated control mice was included in each series of experiments. The mitomycin C treated groups were included as a positive control. A 30 day protocol was employed with the mean survival time in days being determined for each group of mice and the number of survivors at the end of the 30 day period being noted. The mice were weighed before treatment and again on day six. The change in weight was taken as a measure of drug toxicity. Mice weighing 20 grams each were employed and a loss in weight of up to approximately 2 grams was not considered excessive. The results were determined in terms of % T/C which is the ratio of the mean survival time of the treated group to the mean survival time of the saline treated control group times 100. The saline treated control animals usually died within nine days. The "maximum effect" in the following Table is expressed as % T/C and the dose giving that effect is given. The values in parenthesis are the values obtained with mitomycin C as the positive control in the same experiment. Thus a measure of the relative activity of the present substances to mitomycin C can be estimated. A minimum effect in terms of % T/C was considered to be 125. The minimum effective dose reported in the following table is that dose giving a % T/C of approximately 125. The two values given in each instance in the "average weight change" column are respectively the average weight change per mouse at the maximum effective dose and at the minimum effective dose.

TABLE IV

| Compound (Example No) | Inhibition of P-388 Murine Leukemia | | Minimum effective dose | Average weight change[2] |
|---|---|---|---|---|
| | Maximum Effect | | | |
| | % T/C | dose[1] | | |
| V (1) | 311 (244) | 6.4 (3.2) | <0.2 | −1.9, −0.2 |
| | 183 (272) | 6.4 (3.2) | 0.1 | −1.0, +0.3 |
| VI (1) | 233 (244) | 6.4 (3.2) | <0.2 | −0.1, +0.1 |
| VII (2) | 141 (224) | 25.6 (3.2) | 0.8 | −1.2, +0.2 |
| IX (4) | 165 (224) | 12.8 (3.2) | 0.2 | −0.7, +0.8 |
| X (5) | 300 (224) | 12.8 (3.2) | 0.2 | −2.1, none |
| XIII (12) | 161 (211) | 12.8 (3.2) | 3.2 | −0.3, +0.2 |
| XIV (3) | 233 (272) | 12.8 (3.2) | 0.2 | −3.8, +0.7 |
| XV (3) | 144 (272) | 25.6 (3.2) | 6.4 | −1.4, +0.2 |
| XVI (6) | 144 (272) | 6.4 (3.2) | 3.2 | −0.4, −0.3 |
| XVII (7) | 144 (272) | 0.8 (3.2) | 0.02 | −0.2, −0.3 |
| XVIII (7) | 167 (272) | 6.4 (3.2) | 0.05 | −1.0, +0.3 |
| XIX (8) | 333 (294) | 1.6 (3.2) | <0.2 | −1.9, +1.6 |
| | 200 (239) | 0.8 (3.2) | <0.2 | −2.7, −1.8 |
| XX (9) | 333 (294) | 3.2 (3.2) | <0.2 | −2.7, +3.2 |
| XXI (18) | 189 (183) | 1.6 (3.2) | 0.025 | −0.5, −0.1 |
| XXXI (30) | 150 (144) | 6.4 (4.8) | 1.6 | −1.6, −2.3 |
| | 267 (267) | 3.2 (4.8) | <1.6 | −2.3, −1.7 |
| XXX (29) | 206 (263) | 3.2 (4.8) | <3.2 | −1.7, −1.7 |
| XXVI (25) | 183 (239) | 0.4 (3.2) | <0.025 | −3.1, −2.3 |
| XXVII (26) | 144 (239) | 0.2 (3.2) | 0.025 | −1.3, −0.9 |
| XXIII (21) | 194 (319) | 12.8 (3.2) | 0.2 | −1.2, +0.2 |
| XXIV (22) | 313 (319) | 6.4 (3.2) | <0.1 | −2.8, +0.3 |
| XXV (23) | 188 (331) | 25.6 (4.8) | 0.4 | −2.2, +0.1 |
| XXVIII (27) | 119 (313) | 3.2 (3.2) | 3.2 | +2.2, +2.2 |
| XXIX (28) | 331 (319) | 25.6 (3.2) | 0.4 | −2.8, +0.6 |

[1] mg/kg of body weight
[2] grams per mouse, days 1–6, at maximum and minimum effective doses Compounds XIX and XX are of exceptional interest since their activity clearly exceeds that of mitomycin C both in terms of maximum effect and milligram potency (comparative dosage sizes for equivalent effects). They are each compounds of formula I in which A is the said amidino group and B is -$NH_2$, or in other words mitomycin C derivatives substituted at $N^7$ by an aminomethylene group of the formula

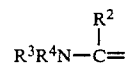

wherein $R^2$, $R^3$, and $R^4$ are as defined above.

The bis-amidino compounds of the present invention of Formula I wherein each of A and B is said amidino group, are also of substantial interest as active antitumor entities. Refer to the data in Table for Compounds V, VI, VII, IX, X, and XIV which conform to this structural requirement.

Table V contains results of antitumor tests using the B16 melanoma grown in mice. $BDF_1$ mice were employed and inoculated intraperitoneally with the tumor implant. A 60 day protocol was used. Groups of ten mice were used for each dosage amount tested and the mean survival time for each group was determined. Control animals inoculated in the same way as the test animals and treated with the injection vehicle and no drug exhibited a mean survival time of 21 days. The survival time relative to that of the controls (% T/C) was used as a measure of effectiveness, and the maximal effective dose and minimal effective dose for each test compound was determined. The minimal effective dose was defined as that dose exhibiting a % T/C value of 125. For each dosage level, the test animals were treated with the test compound on days 1, 5, and 9 by the intraperitoneal route. The average weight change on the day indicated at the maximal effective dose and at the minimal effective was used as a measure of toxicity. A weight loss of 2 g. for a 20 g. mouse was not excessive.

TABLE V

| Compound No. (Example) | Inhibition of B16 Melanoma | | | Average Wt. Change (day) |
|---|---|---|---|---|
| | Maximum Effect % T/C | Dose | Minimum Effective Dose | |
| V (1) | >298 (256)* | 0.8 (3.2)* | <0.2 | +0.5, −0.2 (5) |
| X (5) | >295 (198) | 2.0 (3.0) | <2.0 | −0.4, −0.4 (6) |
| XXI (18) | >295 (198) | 0.4 (3.0) | <0.2 | −0.2, −1.8 (6) |
| XX (9) | 262 (198) | 0.8 (3.0) | <0.2 | −2.6, −1.6 (6) |
| XIX (8) | >235 (165) | 1.2 (3.0) | <0.5 | +0.6, +0.8 (5) |

*values in parenthesis are mitomycin C control values

Compound XXX (Example 29), and Compound XXIX (Example 28), were tested against the B16 murine melanoma employing the subcutaneous route of tumor implant and intravenous drug treatment. The treatment schedule and survival time evaluations (a 40 day protocol was employed) were determined as before. Weight change on day 12 was measured. The maximal effective dose of Compound XXX was 1 mg per kg providing a % T/C 156 and a weight gain of 1.5 g. Groups of six animals were employed and three animals survived the entire 40 day protocol at this dose. The minimal effective dose was 0.25 mg/kg at which dose the 12 day weight change was 1.0 g. For Compound XXIX the maximal effective dose was 8 mg/kg for a % T/C of 177 and a weight change of −0.6. The minimal effective dose was 4 mg/kg with a weight change of +0.8. In the same experiment the maximal effective dose of mitomycin C was 3 mg/kg for a % T/C 195 weight change −0.5. The minimal effective dose of mitomycin C was not determined.

In a brief toxicological protocol using groups of five male BDF$_1$ mice per dose given a single intraperitoneal dose of Compound XIX, no significant reduction in lymphocyte count ocurred at the optimally effective dose of this compound (1.6 mg/kg i.p.). At this dose there was no significant elevation of blood urea nitrogen (BUN) or serum glutamic phospho transferase (SGPT) indicating no adverse effect on kidney or liver function or suppression of lymphcytic activity.

In view of the outstanding antitumor activity observed in experimental animal tumors, and the reduced toxicity compared to mitomycin C, the invention includes use of the substances of formula I for inhibiting mammalian tumors. For this purpose they are administered systemically to a mammal bearing a tumor in substantially non-toxic antitumor effective dose.

What is claimed:
1. A compound having the formula:

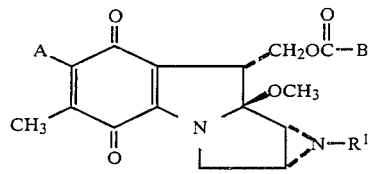

Formula I wherein:
A is amino, methoxy, hydroxy, (1-lower alkyl-2(1H)-pyridinylidene)amino, or a group of the formula

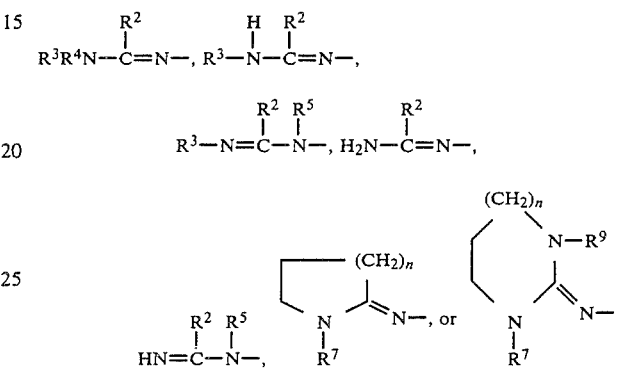

B is amino or the amidino group of the formula

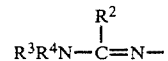

and at least one of A and B is one of the specified groups other than amino, methoxy, or hydroxy,
n is the integer of 0, 1, 2, or 3,
$R^1$ is hydrogen, lower alkyl, lower alkanoyl, benzoyl or substituted benzoyl wherein said substituent is lower alkyl, lower alkoxy, halo, amino, or nitro,
$R^2$ is hydrogen, lower alkyl, phenyl, lower alkylphenyl, lower alkoxyphenyl, halophenyl, aminophenyl, nitrophenyl, thienyl, furyl, cyano, dilower alkylamino, lower alkoxy, or lower alkylthio,
$R^3$ is lower alkyl, or lower alkoxy,
$R^4$ is lower alkyl, or $R^3$ and $R^4$ together with the nitrogen atom to which they are attached constitutes pyrrolidine, 2-, or 3-lower alkylpyrrolidine, piperidine, 2-, 3-, or 4-lower alkylpiperidine, 2,6-dilower alkylpiperidine, piperazine, 4-substituted piperazine (wherein said 4-substituent is alkyl, or carbalkoxy each having 1 to 8 carbon atoms, phenyl, methylphenyl, methoxyphenyl, halophenyl, nitrophenyl, or benzyl), azepine, 2-, 3-, 4-, or 5-lower alkylazepine, morpholine, thiomorpholine, thiomorpholine-1-oxide, or thiomorpholine-1,1-dioxide,
$R^5$ is selected from $C_{1-18}$ alkyl other than tert.-alkyl, $C_{1-18}$ alkenyl, $C_{1-18}$ alkynyl, $C_{1-18}$ haloalkyl, $C_{1-18}$ hydroxyalkyl, $C_{4-8}$ cycloalkyl, or aryl or lower aralkyl, each having up to 12 carbon atoms or a heteroalicyclic or heteroaromatic group having from 3 to 8 ring members at least two of which are carbon atoms,
$R^7$ and $R^9$ are independently H or lower alkyl wherein each of the aforesaid lower alkyl, lower alkanoyl and lower alkoxy groups contains 1 to 6 carbon atoms.

2. The compound of claim 1 wherein A and B are each independently said amidino group of the formula

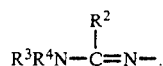

3. The compound of claim 2 wherein $R^1$ and $R^2$ are each hydrogen, and $R^3$ and $R^4$ are each methyl.

4. The compound of claim 1, 7-[(dimethylamino)methylene]amino-$N^{10}$-(dimethylamino)methylene-9a-methoxymitosane.

5. The compound of claim 1, 7-[(dimethylamino)methylene]amino-$N^{10}$-(dimethylamino)methylene-$N^{1a}$-formyl-9a-methoxymitosane.

6. The compound of claim 1, 7-[(diisopropylamino)methylene]amino-$N^{10}$-(diisopropylamino)methylene-9a-methoxymitosane.

7. The compound of claim 1, 7-[(dimethylamino)methylene]amino-$N^{10}$-(dimethylamino)methylene-9a-methoxy-$N^{1a}$-methylmitosane.

8. The compound of claim 2 wherein $R^1$ and $R^2$ are each hydrogen and $R^3$ and $R^4$ together with the nitrogen atom to which they are attached from the piperidine group.

9. The compound of claim 1, $N^{1a}$-formyl-9a-methoxy-7-(1-piperidinylmethylene)amino-$N^{10}$-(1-piperidinylmethylene)mitosane.

10. The compound of claim 1, 9a-methoxy-7-(1-piperidinylmethylene)amino-$N^{10}$-(1-piperidinylmethylene)mitosane.

11. The compound of claim 2 wherein $R^1$ and $R^2$ are each hydrogen and $R^3$ and $R^4$ together with the nitrogen atom to which they are attached from the morpholine group.

12. The compound of claim 1, 9a-methoxy-7-(1-morpholinolmethylene)amino-$N^{10}$-(1-morpholiomethylene)mitosane.

13. The compound of claim 1 wherein A is amino and B is the amidino group of the formula

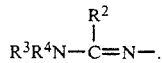

14. The compound of claim 13 wherein $R^3$ and $R^4$ are each methyl.

15. The compound of claim 1, 7-amino-$N^{10}$-dimethylaminomethylene-9a-methoxy-$N^{1a}$-methylmitosane.

16. The compound of claim 1, 7-amino-$N^{10}$-dimethylaminomethylene-9a-methoxymitosane.

17. The compound of claim 1 wherein A is methoxy and B is the amidino group of the formula

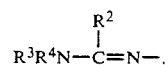

18. The compound of claim 17 wherein $R^3$ and $R^4$ are each methyl.

19. The compound of claim 1, 7,9a-dimethoxy-$N^{10}$-dimethylaminomethylenemitosane.

20. The compound of claim 1, 7,9a-dimethoxy-$N^{10}$-dimethylaminomethylene-$N^{1a}$-formylmitosane.

21. The compound of claim 1 wherein A is one of the said amidino groups and B is amino.

22. The compound of claim 21 wherein A is the amidino group of the formula

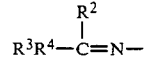

and, $R^3$ and $R^4$ are methyl.

23. The compound of claim 1, 7-(dimethylaminomethylene)amino-9a-methoxymitosane.

24. The compound of claim 1, 7-(dimethylaminomethylene)amino-9a-methoxy-$N^{1a}$-methylmitosane.

25. The compound of claim 1, 7-(1-methyl-2(H)-pyridinylidene)amino-9a-methoxymitosane.

26. The compound of claim 1, 9a-methoxy-7-(1-morpholinomethylene)aminomitosane.

27. The compound of claim 1, 7-(1-pyrrolidinylmethylene)amino-9a-methoxymitosane.

28. The compound of claim 1, 7-[1-(dimethylamino)ethylidene]amino-$N^{10}$-[1-(dimethylamino)ethylidene]-9a-methoxymitosane.

29. The compound of claim 1, 7-[1-(dimethylamino)ethylideneamino]-9a-methoxymitosane.

30. The compound of claim 1, 7-[(1-methyl-2-pyrrolidinylidene)amino]-$N^{10}$-[(1-methyl-2-pyrrolidinylidene)amino]-9a-methoxymitosane.

31. The compound of claim 1, 7-[(1-methyl-2-pyrrolidinylidene)amino]-9a-methoxymitosane.

32. The compound of claim 1, 7-[(methoxyamino)methylene]amino-9a-methoxymitosane.

33. The compound of claim 1, 7-[(benzyloxyamino)methylene]amino-9a-methoxymitosane.

34. The compound of claim 1, 7-(1,3-dimethyl-2-imidazolidylidene)-9a-methoxymitosane.

35. The compound of claim 1, 7-[(1, 3-dimethyltetrahydropyrimidinylidene)amino]-9a-methoxymitosane.

36. The compound of claim 1, 7-(tetramethyldiaminomethylene)amino-9a-methoxymitosane.

37. The compound of claim 1, 7-(1-piperidinylmethylene)amino-9a-methoxymitosane.

38. 7-[2-Benzylthioethyl]amino-9a-methoxymitosane.

39. The method of inhibiting growth of a mammalian tumor which comprising systemic administration to a mammal bearing a tumor, a substantially non-toxic antitumor effective dose of a compound of claim 1.

* * * * *